(12) United States Patent
Kamboj et al.

(10) Patent No.: US 6,403,323 B1
(45) Date of Patent: Jun. 11, 2002

(54) AMPA-BINDING HUMAN GLUR3 RECEPTORS

(75) Inventors: Rajender Kamboj, Mississauga; Candace E. Elliott; Stephen L. Nutt, both of Etobicoke, all of (CA)

(73) Assignee: NPS Allelix Corporation, Mississauga (CA)

( * ) Notice: Subject to any disclaimer, the term of this patent is extended or adjusted under 35 U.S.C. 154(b) by 0 days.

(21) Appl. No.: 08/257,029

(22) Filed: Jun. 8, 1994

Related U.S. Application Data

(62) Division of application No. 07/896,612, filed on Jun. 10, 1992, now abandoned.

(51) Int. Cl.[7] ............................................. C01N 33/53
(52) U.S. Cl. ...................... 435/7.1; 435/7.21; 435/7.2; 435/69.1
(58) Field of Search .............................. 435/6, 7.1, 7.2, 435/7.21, 69.1, 252.3, 320.1; 536/23.5

(56) References Cited

FOREIGN PATENT DOCUMENTS

WO    WO 91/06648    5/1994

OTHER PUBLICATIONS

McNamara et al. "Chromosomal Localization of Human Glutamate Receptor Genes", *Jnl. of Neurosci.*, 12(7):2555–2562, Jul. 1992.

Hollmann et al. Nature 1989 342:643.
Keinanen et al, Science 1990 249:556.
Boulter et al. Science 1990 249:1033.
Bettler et al, Neuron 1990 5:583.
Sommer et al, Science 1990 249:1580.
Monyer et al, Neuron 1991 6:799.
Nakanishi et al, Neuron 1990 5:569.
Hollmann et al, Science 1991 252:851.
Verdoorn et al, Science 1991 252:1715.
Egebjerg et al, Nature 1991 351:745.
Wada et al, Nature 1991 342:684.
Gregor et al, Nature 1989 342:689.
Werner et al, Nature 1991 351:742.
Barnett et al, Nucleic Acids Res. 1990 18(10):3094.
William Sun, et al., "Molecular Cloning, Chromosomal Mapping, and Functional Expression of Human Brain Glutamate Receptors", Proc. Natl. Acad. Sci. USA, vol. 89, pp. 1443–1447, Feb. 1992.
C. Puckett, et al., "Molecular Cloning and Chromosomal Localization of One of the Human Glutamate Receptor Genes", Proc. Natl. Acad. Sci. USA, vol. 88, pp. 7557–7561, Sep. 1991.

*Primary Examiner*—John Ulm
(74) *Attorney, Agent, or Firm*—Foley & Lardner

(57) ABSTRACT

Described herein are isolated polynucleotides which code for a family of AMPA-type human CNS receptors. The receptors are characterized structurally and the construction and use of cell lines expressing these receptors are disclosed.

7 Claims, 16 Drawing Sheets

FIG. 1A

EcoRI
|

```
      gaattcctgacgactcctgagttgcgcccatgctcttgtcagcttcgttttaggcgtagc
  1   ----------+----------+----------+----------+----------+----------+  60
      cttaaggactgctgaggactcaacgcgggtacgagaacagtcgaagcaaaatccgcatcg atggccaggcagaagaaaatggggcaaagcgtgctccgggcggtcttcttttttagtcctg
 61   ----------+----------+----------+----------+----------+----------+ 120
      taccggtccgtcttcttttacccgtttcgcacgaggcccgccagaagaaaaatcaggac

M  G  Q  S  V  L  R  A  V  F  F  L  V  L  - gggcttttgggtcattctcacggaggattccccaacaccatcagcataggtggacttttc
121   ----------+----------+----------+----------+----------+----------+ 180
      cccgaaaacccagtaagagtgcctcctaaggggttgtggtagtcgtatccacctgaaaag G  L  L  G  H  S  H  G  G  F  P  N  T  I  S  I  G  G  L  F  -
                                 |_Mature N-Terminal atgagaaacacagtgcaggagcacagcgctttccgctttgccgtgcagttatacaacacc
181   ----------+----------+----------+----------+----------+----------+ 240
      tactctttgtgtcacgtcctcgtgtcgcgaaaggcgaaacggcacgtcaatatgttgtgg

M  R  N  T  V  Q  E  H  S  A  F  R  F  A  V  Q  L  Y  N  T  - aaccagaacaccaccgagaagcccttccatttgaattaccacgtagatcacttggattcc
241   ----------+----------+----------+----------+----------+----------+ 300
      ttggtcttgtggtggctcttcgggaaggtaaacttaatggtgcatctagtgaacctaagg

N  Q  N  T  T  E  K  P  F  H  L  N  Y  H  V  D  H  L  D  S  - tccaatagttttttccgtgacaaatgctttctgctcccagttctcgagagggggtgtatgcc
301   ----------+----------+----------+----------+----------+----------+ 360
      aggttatcaaaaaggcactgtttacgaaagacgagggtcaagagctctccccacatacgg

S  N  S  F  S  V  T  N  A  F  C  S  Q  F  S  R  G  V  Y  A  - atctttggattctatgaccagatgtcaatgaacaccctgacctccttctgtggggccctg
361   ----------+----------+----------+----------+----------+----------+ 420
      tagaaacctaagatactggtctacagttacttgtgggactggaggaagacaccccgggac

I  F  G  F  Y  D  Q  M  S  M  N  T  L  T  S  F  C  G  A  L  - cacacatcctttgttacgcctagcttcccccactgacgcagatgtgcagtttgtcatccag
421   ----------+----------+----------+----------+----------+----------+ 480
      gtgtgtaggaaacaatgcggatcgaaggggtgactgcgtctacacgtcaaacagtaggtc

H  T  S  F  V  T  P  S  F  P  T  D  A  D  V  Q  F  V  I  Q  - atgcgcccagccttgaagggcgctattctgagtcttctgggtcattacaagtgggagaag
481   ----------+----------+----------+----------+----------+----------+ 540
      tacgcgggtcggaacttcccgcgataagactcagaagacccagtaatgttcaccctcttc

M  R  P  A  L  K  G  A  I  L  S  L  L  G  H  Y  K  W  E  K  - tttgtgtacctctatgacacagaacgaggattttccatcctccaagcgattatggaagca
541   ----------+----------+----------+----------+----------+----------+ 600
      aaacacatggagatactgtgtcttgctcctaaaaggtaggaggttcgctaataccttcgt

```
    gcagtgcaaaacaactggcaagtaacagcaaggtctgtgggaaacataaaggacgtccaa
601 ---------+---------+---------+---------+---------+---------+ 660
    cgtcacgttttgttgaccgttcattgtcgttccagacacccttttgtatttcctgcaggtt

A  V  Q  N  N  W  Q  V  T  A  R  S  V  G  N  I  K  D  V  Q   -
```

EcoRI
|
```
    gaattcaggcgcatcattgaagaaatggacaggaggcaggaaaagcgatacttgattgac
661 ---------+---------+---------+---------+---------+---------+ 720
    cttaagtccgcgtagtaacttctttacctgtcctccgtccttttcgctatgaactaactg

E  F  R  R  I  I  E  E  M  D  R  R  Q  E  K  R  Y  L  I  D   - tgcgaagtcgaaaggattaacacaatttttggaacaggttgtgatcctagggaaacactca
721 ---------+---------+---------+---------+---------+---------+ 780
    acgcttcagctttcctaattgtgttaaaaccttgtccaacactaggatccctttgtgagt

C  E  V  E  R  I  N  T  I  L  E  Q  V  V  I  L  G  K  H  S   - agaggttatcactacatgctcgctaacctgggttttactgatatttactggaaagagtc
781 ---------+---------+---------+---------+---------+---------+ 840
    tctccaatagtgatgtacgagcgattggacccaaaatgactataaaatgaccttttctcag

R  G  Y  H  Y  M  L  A  N  L  G  F  T  D  I  L  L  E  R  V   - atgcatgggggagccaacattacaggtttccagattgtcaacaatgaaaaccctatggtt
841 ---------+---------+---------+---------+---------+---------+ 900
    tacgtaccccctcggttgtaatgtccaaaggtctaacagttgttacttttgggataccaa

M  H  G  G  A  N  I  T  G  F  Q  I  V  N  N  E  N  P  M  V   -
```

EcoRI
|
```
    cagcagttcatacagcgctgggtgaggctggatgaaagggaattccctgaagccaagaat
901 ---------+---------+---------+---------+---------+---------+ 960
    gtcgtcaagtatgtcgcgacccactccgacctactttcccttaagggacttcggttctta

Q  Q  F  I  Q  R  W  V  R  L  D  E  R  E  F  P  E  A  K  N   -
```

HindIII
|
```
    gcaccactaaagtatacatctgcattgacacacgacgcaatactggtcatagcagaagct
961 ---------+---------+---------+---------+---------+---------+ 1020
    cgtggtgatttcatatgtagacgtaactgtgtgctgcgttatgaccagtatcgtcttcga

A  P  L  K  Y  T  S  A  L  T  H  D  A  I  L  V  I  A  E  A   - ttccgctacctgaggaggcagcgagtagatgtgtcccggagaggaagtgctggagactgc
1021 ---------+---------+---------+---------+---------+---------+ 1080
    aaggcgatggactcctccgtcgctcatctacacagggcctctccttcacgacctctgacg

F  R  Y  L  R  R  Q  R  V  D  V  S  R  R  G  S  A  G  D  C   - ttagcaaatcctgctgtgccctggagtcaaggaattgatattgagagagctctgaaaatg
1081 ---------+---------+---------+---------+---------+---------+ 1140
    aatcgtttaggacgacacgggacctcagttccttaactataactctctcgagacttttac

```
      gtgcaagtacaaggaatgactggaaatattcaatttgacacttatggacgtaggacaaat
1141  ------------+----------+----------+----------+----------+----------+ 1200
      cacgttcatgttccttactgacctttataagttaaactgtgaatacctgcatcctgttta

V  Q  V  Q  G  M  T  G  N  I  Q  F  D  T  Y  G  R  R  T  N  - tataccatcgatgtgtatgaaatgaaagtcagtggctctcgaaaagctggctactggaac
1201  ------------+----------+----------+----------+----------+----------+ 1260
      atatggtagctacacatactttactttcagtcaccgagagcttttcgaccgatgaccttg

Y  T  I  D  V  Y  E  M  K  V  S  G  S  R  K  A  G  Y  W  N  - gagtatgaaaggtttgtgcctttctcagatcagcaaatcagcaatgacagtgcatcctca
1261  ------------+----------+----------+----------+----------+----------+ 1320
      ctcatactttccaaacacggaaagagtctagtcgtttagtcgttactgtcacgtaggagt

E  Y  E  R  F  V  P  F  S  D  Q  Q  I  S  N  D  S  A  S  S  - gagaatcggaccatagtagtgactaccattctggaatcaccatatgtaatgtacaagaag
1321  ------------+----------+----------+----------+----------+----------+ 1380
      ctcttagcctggtatcatcactgatggtaagaccttagtggtatacattacatgttcttc

E  N  R  T  I  V  V  T  T  I  L  E  S  P  Y  V  M  Y  K  K  - aaccatgagcaactggaaggaaatgaacgatatgaaggctattgtgtagacctagcctat
1381  ------------+----------+----------+----------+----------+----------+ 1440
      ttggtactcgttgaccttcctttacttgctatacttccgataacacatctggatcggata

N  H  E  Q  L  E  G  N  E  R  Y  E  G  Y  C  V  D  L  A  Y  - gaaatagccaaacatgtaaggatcaaatacaaattgtccatcgttggtgacgggaaatat
1441  ------------+----------+----------+----------+----------+----------+ 1500
      ctttatcggtttgtacattcctagtttatgtttaacaggtagcaaccactgcccttttata

E  I  A  K  H  V  R  I  K  Y  K  L  S  I  V  G  D  G  K  Y  - ggtgcaagggatccagagactaaaatatggaacggcatggttggggaacttgtctatggg
1501  ------------+----------+----------+----------+----------+----------+ 1560
      ccacgttccctaggtctctgattttataccttgccgtaccaacccccttgaacagatacccc

G  A  R  D  P  E  T  K  I  W  N  G  M  V  G  E  L  V  Y  G  - agagctgatatagctgttgctccactcactataacattggtccgtgaagaagtcatagat
1561  ------------+----------+----------+----------+----------+----------+ 1620
      tctcgactatatcgacaacgaggtgagtgatattgtaaccaggcacttcttcagtatcta

R  A  D  I  A  V  A  P  L  T  I  T  L  V  R  E  E  V  I  D  - ttttcaaagccattaatgagcctgggcatctccatcatgataaagaagcctcagaaatca
1621  ------------+----------+----------+----------+----------+----------+ 1680
      aaaagtttcggtaattactcggacccgtagaggtagtactattcttcggagtctttagt

F  S  K  P  L  M  S  L  G  I  S  I  M  I  K  K  P  Q  K  S  - aaaccaggcgtattctcatttctggatcccctggcttatgaaatctggatgtgcattgtc
1681  ------------+----------+----------+----------+----------+----------+ 1740
      tttggtccgcataagagtaaagacctaggggaccgaatactttagacctacacgtaacag

```
      tttgcttacattggagtcagcgtagttcttttcctagtcagcaggttcagtccttatgaa
1741  ------------+----------+----------+----------+----------+----------+  1800
      aaacgaatgtaacctcagtcgcatcaagaaaaggatcagtcgtccaagtcaggaatactt F   A   Y   I   G   V   S   V   V   L   F   L   V   S   R   F   S   P   Y   E   - tggcacttggaagacaacaatgaagaacctcgtgacccacaaagtcctcctgatcctcca
1801  ------------+----------+----------+----------+----------+----------+  1860
      accgtgaaccttctgttgttacttcttggagcactgggtgtttcaggaggactaggaggt W   H   L   E   D   N   N   E   E   P   R   D   P   Q   S   P   P   D   P   P   - aatgaatttggaatatttaacagtctttggttttccttgggtgcctttatgcagcaagga
1861  ------------+----------+----------+----------+----------+----------+  1920
      ttacttaaaccttataaattgtcagaaaccaaaaggaacccacggaaatacgtcgttcct N   E   F   G   I   F   N   S   L   W   F   S   L   G   A   F   M   Q   Q   G   - tgtgatatttctccaagatcactctccgggcgcattgttggaggggtttggtggttcttc
1921  ------------+----------+----------+----------+----------+----------+  1980
      acactataaagaggttctagtgagaggcccgcgtaacaacctccccaaaccaccaagaag C   D   I   S   P   R   S   L   S   G   R   I   V   G   G   V   W   W   F   F   - accctgatcataatttcttcctatactgccaatctcgctgctttcctgactgtggagagg
1981  ------------+----------+----------+----------+----------+----------+  2040
      tgggactagtattaaagaaggatatgacggttagagcgacgaaaggactgacacctctcc T   L   I   I   I   S   S   Y   T   A   N   L   A   A   F   L   T   V   E   R   - atggtttctcccatagagagtgctgaagacttagctaaacagactgaaattgcatatggg
2041  ------------+----------+----------+----------+----------+----------+  2100
      taccaaagagggtatctctcacgacttctgaatcgatttgtctgactttaacgtataccc M   V   S   P   I   E   S   A   E   D   L   A   K   Q   T   E   I   A   Y   G   - accctggactccggttcaacaaaagaatttttcagaagatccaaaattgctgtgtacgag
2101  ------------+----------+----------+----------+----------+----------+  2160
      tgggacctgaggccaagttgttttcttaaaaagtcttctaggttttaacgacacatgctc T   L   D   S   G   S   T   K   E   F   F   R   R   S   K   I   A   V   Y   E   - aaaatgtggtcttacatgaaatcagcggagccatctgtgtttaccaaaacaacagcagac
2161  ------------+----------+----------+----------+----------+----------+  2220
      ttttacaccagaatgtactttagtcgcctcggtagacacaaatggttttgttgtcgtctg K   M   W   S   Y   M   K   S   A   E   P   S   V   F   T   K   T   T   A   D   - ggagtggcccgagtgcgaaagtccaagggaaagttcgccttcctgctggagtcaaccatg
2221  ------------+----------+----------+----------+----------+----------+  2280
      cctcaccgggctcacgctttcaggttcccctttcaagcggaaggacgacctcagttggtac G   V   A   R   V   R   K   S   K   G   K   F   A   F   L   L   E   S   T   M   - aatgagtacattgagcagagaaaaccatgtgatacgatgaaagttggtggaaatctggat
2281  ------------+----------+----------+----------+----------+----------+  2340
      ttactcatgtaactcgtctcttttggtacactatgctactttcaaccaccttagaccta N   E   Y   I   E   Q   R   K   P   C   D   T   M   K   V   G   G   N   L   D   -
```

FIG. 1E

```
      tccaaaggctatggtgtgtggcaaccccctaaaggctcagcattaggaaatgctgttaacctg
2341  ----------+---------+---------+---------+---------+---------+  2400
      aggtttccgataccacaccgttggggatttccgagtcgtaatcctttacgacaattggac S  K  G  Y  G  V  A  T  P  K  G  S  A  L  G  N  A  V  N  L
                                StuI
                                  |
      gcagtattaaaactgaatgagcaaggcctcttggacaaattgaaaaacaaatggtggtac
2401  ----------+---------+---------+---------+---------+---------+  2460
      cgtcataattttgacttactcgttccggagaacctgtttaacttttgtttaccaccatg

A  V  L  K  L  N  E  Q  G  L  L  D  K  L  K  N  K  W  W  Y  - gacaaaggagagtgcggcagcggggggcggtgactccaaggacaagaccagcgctctgagc
2461  ----------+---------+---------+---------+---------+---------+  2520
      ctgtttcctctcacgccgtcgccccgccactgaggttcctgttctggtcgcgagactcg

D  K  G  E  C  G  S  G  G  G  D  S  K  D  K  T  S  A  L  S  - ctgagcaatgtggcaggcgttttctatatacttgtcggaggtctggggctggccatgatg
2521  ----------+---------+---------+---------+---------+---------+  2580
      gactcgttacaccgtccgcaaaagatatatgaacagcctccagaccccgaccggtactac L  S  N  V  A  G  V  F  Y  I  L  V  G  G  L  G  L  A  M  M  -
                   EcoRI
                     |
      gtggctttgatagaattctgttacaaatcacgggcagagtccaaacgcatgaaactcaca
2581  ----------+---------+---------+---------+---------+---------+  2640
      caccgaaactatcttaagacaatgtttagtgcccgtctcaggtttgcgtactttgagtgt

V  A  L  I  E  F  C  Y  K  S  R  A  E  S  K  R  M  K  L  T  - aagaacacccaaaactttaagcctgctcctgccaccaacactcagaattatgctacatac
2641  ----------+---------+---------+---------+---------+---------+  2700
      ttcttgtgggttttgaaattcggacgaggacggtggttgtgagtcttaatacgatgtatg

K  N  T  Q  N  F  K  P  A  P  A  T  N  T  Q  N  Y  A  T  Y  - agagaaggctacaacgtgtatggaacagagagtgttaagatctagggatcccttggaatt
2701  ----------+---------+---------+---------+---------+---------+  2760
      tctcttccgatgttgcacataccttgtctctcacaattctagatccctagggaaccttaa

```
    EcoRI
    |
    GAATTCCTGACGACTCCTGAGTTGCGCCCATGCTCTTGTCAGCTTCGTTTTAGGCGTAGC
1   ------------+---------+---------+---------+---------+---------+ 60
    CTTAAGGACTGCTGAGGACTCAACGCGGGTACGAGAACAGTCGAAGCAAAATCCGCATCG

ATGGCCAGGCAGAAGAAAATGGGGCAAAGCGTGCTCCGGGCGGTCTTCTTTTTAGTCCTG
61  ------------+---------+---------+---------+---------+---------+ 120
    TACCGGTCCGTCTTCTTTTACCCCGTTTCGCACGAGGCCCGCCAGAAGAAAAATCAGGAC

M  G  Q  S  V  L  R  A  V  F  F  L  V  L  -

GGGCTTTTGGGTCATTCTCACGGAGGATTCCCCAACACCATCAGCATAGGTGGACTTTTC
121 ------------+---------+---------+---------+---------+---------+ 180
    CCCGAAAACCCAGTAAGAGTGCCTCCTAAGGGGTTGTGGTAGTCGTATCCACCTGAAAAG a    G  L  L  G  H  S  H  G  G  F  P  N  T  I  S  I  G  G  L  F  -
                            |_Mature N-Terminal ATGAGAAACACAGTGCAGGAGCACAGCGCTTTCCGCTTTGCCGTGCAGTTATACAACACC
181 ------------+---------+---------+---------+---------+---------+ 240
    TACTCTTTGTGTCACGTCCTCGTGTCGCGAAAGGCGAAACGGCACGTCAATATGTTGTGG a    M  R  N  T  V  Q  E  H  S  A  F  R  F  A  V  Q  L  Y  N  T  -

AACCAGAACACCACCGAGAAGCCCTTCCATTTGAATTACCACGTAGATCACTTGGATTCC
241 ------------+---------+---------+---------+---------+---------+ 300
    TTGGTCTTGTGGTGGCTCTTCGGGAAGGTAAACTTAATGGTGCATCTAGTGAACCTAAGG a    N  Q  N  T  T  E  K  P  F  H  L  N  Y  H  V  D  H  L  D  S  -

TCCAATAGTTTTTCCGTGACAAATGCTTTCTGCTCCCAGTTCTCGAGAGGGGTGTATGCC
301 ------------+---------+---------+---------+---------+---------+ 360
    AGGTTATCAAAAAGGCACTGTTTACGAAAGACGAGGGTCAAGAGCTCTCCCCACATACGG a    S  N  S  F  S  V  T  N  A  F  C  S  Q  F  S  R  G  V  Y  A  -

ATCTTTGGATTCTATGACCAGATGTCAATGAACACCCTGACCTCCTTCTGTGGGGCCCTG
361 ------------+---------+---------+---------+---------+---------+ 420
    TAGAAACCTAAGATACTGGTCTACAGTTACTTGTGGGACTGGAGGAAGACACCCCGGGAC a    I  F  G  F  Y  D  Q  M  S  M  N  T  L  T  S  F  C  G  A  L  -

CACACATCCTTTGTTACGCCTAGCTTCCCCACTGACGCAGATGTGCAGTTTGTCATCCAG
421 ------------+---------+---------+---------+---------+---------+ 480
    GTGTGTAGGAAACAATGCGGATCGAAGGGGTGACTGCGTCTACACGTCAAACAGTAGGTC a    H  T  S  F  V  T  P  S  F  P  T  D  A  D  V  Q  F  V  I  Q  -
```

FIG. 3B

```
     ATGCGCCCAGCCTTGAAGGGCGCTATTCTGAGTCTTCTGGGTCATTACAAGTGGGAGAAG
481  ------------+---------+---------+---------+---------+---------+ 540
     TACGCGGGTCGGAACTTCCCGCGATAAGACTCAGAAGACCCAGTAATGTTCACCCTCTTC a    M  R  P  A  L  K  G  A  I  L  S  L  L  G  H  Y  K  W  E  K   -

TTTGTGTACCTCTATGACACAGAACGAGGATTTTCCATCCTCCAAGCGATTATGGAAGCA
541  ------------+---------+---------+---------+---------+---------+ 600
     AAACACATGGAGATACTGTGTCTTGCTCCTAAAAGGTAGGAGGTTCGCTAATACCTTCGT a    F  V  Y  L  Y  D  T  E  R  G  F  S  I  L  Q  A  I  M  E  A   -

GCAGTGCAAAACAACTGGCAAGTAACAGCAAGGTCTGTGGGAAACATAAAGGACGTCCAA
601  ------------+---------+---------+---------+---------+---------+ 660
     CGTCACGTTTTGTTGACCGTTCATTGTCGTTCCAGACACCCTTTGTATTTCCTGCAGGTT a    A  V  Q  N  N  W  Q  V  T  A  R  S  V  G  N  I  K  D  V  Q   -

EcoRI
          |
     GAATTCAGGCGCATCATTGAAGAAATGGACAGGAGGCAGGAAAAGCGATACTTGATTGAC
661  ------------+---------+---------+---------+---------+---------+ 720
     CTTAAGTCCGCGTAGTAACTTCTTTACCTGTCCTCCGTCCTTTTCGCTATGAACTAACTG a    E  F  R  R  I  I  E  E  M  D  R  R  Q  E  K  R  Y  L  I  D   -

TGCGAAGTCGAAAGGATTAACACAATTTTGGAACAGGTTGTGATCCTAGGGAAACACTCA
721  ------------+---------+---------+---------+---------+---------+ 780
     ACGCTTCAGCTTTCCTAATTGTGTTAAAACCTTGTCCAACACTAGGATCCCTTTGTGAGT a    C  E  V  E  R  I  N  T  I  L  E  Q  V  V  I  L  G  K  H  S   -

AGAGGTTATCACTACATGCTCGCTAACCTGGGTTTTACTGATATTTTACTGGAAAGAGTC
781  ------------+---------+---------+---------+---------+---------+ 840
     TCTCCAATAGTGATGTACGAGCGATTGGACCCAAAATGACTATAAAATGACCTTTCTCAG a    R  G  Y  H  Y  M  L  A  N  L  G  F  T  D  I  L  L  E  R  V   -

ATGCATGGGGGAGCCAACATTACAGGTTTCCAGATTGTCAACAATGAAAACCCTATGGTT
841  ------------+---------+---------+---------+---------+---------+ 900
     TACGTACCCCCTCGGTTGTAATGTCCAAAGGTCTAACAGTTGTTACTTTTGGGATACCAA a    M  H  G  G  A  N  I  T  G  F  Q  I  V  N  N  E  N  P  M  V   -

EcoRI
                                                 |
     CAGCAGTTCATACAGCGCTGGGTGAGGCTGGATGAAAGGGAATTCCCTGAAGCCAAGAAT
901  ------------+---------+---------+---------+---------+---------+ 960
     GTCGTCAAGTATGTCGCGACCCACTCCGACCTACTTTCCCTTAAGGGACTTCGGTTCTTA a    Q  Q  F  I  Q  R  W  V  R  L  D  E  R  E  F  P  E  A  K  N   -

HindIII
                                                      |
     GCACCACTAAAGTATACATCTGCATTGACACACGACGCAATACTGGTCATAGCAGAAGCT
961  ------------+---------+---------+---------+---------+---------+ 1020
     CGTGGTGATTTCATATGTAGACGTAACTGTGTGCTGCGTTATGACCAGTATCGTCTTCGA a    A  P  L  K  Y  T  S  A  L  T  H  D  A  I  L  V  I  A  E  A   -
```

FIG. 3C

```
       TTCCGCTACCTGAGGAGGCAGCGAGTAGATGTGTCCCGGAGAGGAAGTGCTGGAGACTGC
1021   ------------+----------+----------+----------+----------+----------+ 1080
       AAGGCGATGGACTCCTCCGTCGCTCATCTACACAGGGCCTCTCCTTCACGACCTCTGACG a      F  R  Y  L  R  R  Q  R  V  D  V  S  R  R  G  S  A  G  D  C    -

TTAGCAAATCCTGCTGTGCCCTGGAGTCAAGGAATTGATATTGAGAGAGCTCTGAAAATG
1081   ------------+----------+----------+----------+----------+----------+ 1140
       AATCGTTTAGGACGACACGGGACCTCAGTTCCTTAACTATAACTCTCTCGAGACTTTTAC a      L  A  N  P  A  V  P  W  S  Q  G  I  D  I  E  R  A  L  K  M    -

GTGCAAGTACAAGGAATGACTGGAAATATTCAATTTGACACTTATGGACGTAGGACAAAT
1141   ------------+----------+----------+----------+----------+----------+ 1200
       CACGTTCATGTTCCTTACTGACCTTTATAAGTTAAACTGTGAATACCTGCATCCTGTTTA a      V  Q  V  Q  G  M  T  G  N  I  Q  F  D  T  Y  G  R  R  T  N    -

TATACCATCGATGTGTATGAAATGAAAGTCAGTGGCTCTCGAAAAGCTGGCTACTGGAAC
1201   ------------+----------+----------+----------+----------+----------+ 1260
       ATATGGTAGCTACACATACTTTACTTTCAGTCACCGAGAGCTTTTCGACCGATGACCTTG a      Y  T  I  D  V  Y  E  M  K  V  S  G  S  R  K  A  G  Y  W  N    -

GAGTATGAAAGGTTTGTGCCTTTCTCAGATCAGCAAATCAGCAATGACAGTGCATCCTCA
1261   ------------+----------+----------+----------+----------+----------+ 1320
       CTCATACTTTCCAAACACGGAAAGAGTCTAGTCGTTTAGTCGTTACTGTCACGTAGGAGT a      E  Y  E  R  F  V  P  F  S  D  Q  Q  I  S  N  D  S  A  S  S    -

GAGAATCGGACCATAGTAGTGACTACCATTCTGGAATCACCATATGTAATGTACAAGAAG
1321   ------------+----------+----------+----------+----------+----------+ 1380
       CTCTTAGCCTGGTATCATCACTGATGGTAAGACCTTAGTGGTATACATTACATGTTCTTC a      E  N  R  T  I  V  V  T  T  I  L  E  S  P  Y  V  M  Y  K  K    -

AACCATGAGCAACTGGAAGGAAATGAACGATATGAAGGCTATTGTGTAGACCTAGCCTAT
1381   ------------+----------+----------+----------+----------+----------+ 1440
       TTGGTACTCGTTGACCTTCCTTTACTTGCTATACTTCCGATAACACATCTGGATCGGATA a      N  H  E  Q  L  E  G  N  E  R  Y  E  G  Y  C  V  D  L  A  Y    -

GAAATAGCCAAACATGTAAGGATCAAATACAAATTGTCCATCGTTGGTGACGGGAAATAT
1441   ------------+----------+----------+----------+----------+----------+ 1500
       CTTTATCGGTTTGTACATTCCTAGTTTATGTTTAACAGGTAGCAACCACTGCCCTTTATA a      E  I  A  K  H  V  R  I  K  Y  K  L  S  I  V  G  D  G  K  Y    -

GGTGCAAGGGATCCAGAGACTAAAATATGGAACGGCATGGTTGGGGAACTTGTCTATGGG
1501   ------------+----------+----------+----------+----------+----------+ 1560
       CCACGTTCCCTAGGTCTCTGATTTTATACCTTGCCGTACCAACCCCTTGAACAGATACCC a      G  A  R  D  P  E  T  K  I  W  N  G  M  V  G  E  L  V  Y  G    -

AGAGCTGATATAGCTGTTGCTCCACTCACTATAACATTGGTCCGTGAAGAAGTCATAGAT
1561   ------------+----------+----------+----------+----------+----------+ 1620
       TCTCGACTATATCGACAACGAGGTGAGTGATATTGTAACCAGGCACTTCTTCAGTATCTA a      R  A  D  I  A  V  A  P  L  T  I  T  L  V  R  E  E  V  I  D    -
```

FIG. 3D

```
        TTTTCAAAGCCATTAATGAGCCTGGGCATCTCCATCATGATAAAGAAGCCTCAGAAATCA
  1621  ------------+----------+----------+----------+----------+----------+  1680
        AAAAGTTTCGGTAATTACTCGGACCCGTAGAGGTAGTACTATTTCTTCGGAGTCTTTAGT a        F  S  K  P  L  M  S  L  G  I  S  I  M  I  K  K  P  Q  K  S   -

AAACCAGGCGTATTCTCATTTCTGGATCCCCTGGCTTATGAAATCTGGATGTGCATTGTC
  1681  ------------+----------+----------+----------+----------+----------+  1740
        TTTGGTCCGCATAAGAGTAAAGACCTAGGGGACCGAATACTTTAGACCTACACGTAACAG a        K  P  G  V  F  S  F  L  D  P  L  A  Y  E  I  W  M  C  I  V   -

TTTGCTTACATTGGAGTCAGCGTAGTTCTTTTCCTAGTCAGCAGGTTCAGTCCTTATGAA
  1741  ------------+----------+----------+----------+----------+----------+  1800
        AAACGAATGTAACCTCAGTCGCATCAAGAAAAGGATCAGTCGTCCAAGTCAGGAATACTT a        F  A  Y  I  G  V  S  V  V  L  F  L  V  S  R  F  S  P  Y  E   -

TGGCACTTGGAAGACAACAATGAAGAACCTCGTGACCCACAAAGTCCTCCTGATCCTCCA
  1801  ------------+----------+----------+----------+----------+----------+  1860
        ACCGTGAACCTTCTGTTGTTACTTCTTGGAGCACTGGGTGTTTCAGGAGGACTAGGAGGT a        W  H  L  E  D  N  N  E  E  P  R  D  P  Q  S  P  P  D  P  P   -

AATGAATTTGGAATATTTAACAGTCTTTGGTTTTCCTTGGGTGCCTTTATGCAGCAAGGA
  1861  ------------+----------+----------+----------+----------+----------+  1920
        TTACTTAAACCTTATAAATTGTCAGAAACCAAAAGGAACCCACGGAAATACGTCGTTCCT a        N  E  F  G  I  F  N  S  L  W  F  S  L  G  A  F  M  Q  Q  G   -

TGTGATATTTCTCCAAGATCACTCTCCGGGCGCATTGTTGGAGGGGTTTGGTGGTTCTTC
  1921  ------------+----------+----------+----------+----------+----------+  1980
        ACACTATAAAGAGGTTCTAGTGAGAGGCCCGCGTAACAACCTCCCCAAACCACCAAGAAG a        C  D  I  S  P  R  S  L  S  G  R  I  V  G  G  V  W  W  F  F   -

ACCCTGATCATAATTTCTTCCTATACTGCCAATCTCGCTGCTTTCCTGACTGTGGAGAGG
  1981  ------------+----------+----------+----------+----------+----------+  2040
        TGGGACTAGTATTAAAGAAGGATATGACGGTTAGAGCGACGAAAGGACTGACACCTCTCC a        T  L  I  I  I  S  S  Y  T  A  N  L  A  A  F  L  T  V  E  R   -

ATGGTTTCTCCCATAGAGAGTGCTGAAGACTTAGCTAAACAGACTGAAATTGCATATGGG
  2041  ------------+----------+----------+----------+----------+----------+  2100
        TACCAAAGAGGGTATCTCTCACGACTTCTGAATCGATTTGTCTGACTTTAACGTATACCC a        M  V  S  P  I  E  S  A  E  D  L  A  K  Q  T  E  I  A  Y  G   -

ACCCTGGACTCCGGTTCAACAAAAGAATTTTTCAGAAGATCCAAAATTGCTGTGTACGAG
  2101  ------------+----------+----------+----------+----------+----------+  2160
        TGGGACCTGAGGCCAAGTTGTTTTCTTAAAAAGTCTTCTAGGTTTTAACGACACATGCTC a        T  L  D  S  G  S  T  K  E  F  F  R  R  S  K  I  A  V  Y  E   -

AAAATGTGGTCTTACATGAAATCAGCGGAGCCATCTGTGTTTACCAAAACAACAGCAGAC
  2161  ------------+----------+----------+----------+----------+----------+  2220
        TTTTACACCAGAATGTACTTTAGTCGCCTCGGTAGACACAAATGGTTTTGTTGTCGTCTG a        K  M  W  S  Y  M  K  S  A  E  P  S  V  F  T  K  T  T  A  D   -
```

FIG. 3E

```
         GGAGTGGCCCGAGTGCGAAAGTCCAAGGGAAAGTTCGCCTTCCTGCTGGAGTCAACCATG
    2221 ------------+----------+----------+----------+----------+----------+ 2280
         CCTCACCGGGCTCACGCTTTCAGGTTCCCTTTCAAGCGGAAGGACGACCTCAGTTGGTAC a        G  V  A  R  V  R  K  S  K  G  K  F  A  F  L  L  E  S  T  M    -

AATGAGTACATTGAGCAGAGAAAACCATGTGATACGATGAAAGTTGGTGGAAATCTGGAT
    2281 ------------+----------+----------+----------+----------+----------+ 2340
         TTACTCATGTAACTCGTCTCTTTTGGTACACTATGCTACTTTCAACCACCTTTAGACCTA a        N  E  Y  I  E  Q  R  K  P  C  D  T  M  K  V  G  G  N  L  D    -

TCCAAAGGCTATGGTGTGGCAACCCCTAAAGGCTCAGCATTAGGAACGCCTGTAAACCTT
    2341 ------------+----------+----------+----------+----------+----------+ 2400
         AGGTTTCCGATACCACACCGTTGGGGATTTCCGAGTCGTAATCCTTGCGGACATTTGGAA a        S  K  G  Y  G  V  A  T  P  K  G  S  A  L  G  T  P  V  N  L    -

GCAGTATTGAAACTCAGTGAACAAGGCATCTTAGACAAGCTGAAAAACAAATGGTGGTAC
    2401 ------------+----------+----------+----------+----------+----------+ 2460
         CGTCATAACTTTGAGTCACTTGTTCCGTAGAATCTGTTCGACTTTTTGTTTACCACCATG a        A  V  L  K  L  S  E  Q  G  I  L  D  K  L  N  K  W  W  Y    -

GATAAGGGGGAATGTGGAGCCAAGGACTCCGGGAGTAAGGACAAGACCAGCGCTCTGAGC
    2461 ------------+----------+----------+----------+----------+----------+ 2520
         CTATTCCCCCTTACACCTCGGTTCCTGAGGCCCTCATTCCTGTTCTGGTCGCGAGACTCG a        D  K  G  E  C  G  A  K  D  S  G  S  K  D  K  T  S  A  L  S    -

CTGAGCAATGTGGCAGGCGTTTTCTATATACTTGTCGGAGGTCTGGGGCTGGCCATGATG
    2521 ------------+----------+----------+----------+----------+----------+ 2580
         GACTCGTTACACCGTCCGCAAAAGATATATGAACAGCCTCCAGACCCCGACCGGTACTAC a        L  S  N  V  A  G  V  F  Y  I  L  V  G  G  L  G  L  A  M  M    -

EcoRI
                               |
         GTGGCTTTGATAGAATTCTGTTACAAATCACGGGCAGAGTCCAAACGCATGAAACTCACA
    2581 ------------+----------+----------+----------+----------+----------+ 2640
         CACCGAAACTATCTTAAGACAATGTTTAGTGCCCGTCTCAGGTTTGCGTACTTTGAGTGT a        V  A  L  I  E  F  C  Y  K  S  R  A  E  S  K  R  M  K  L  T    -

AAGAACACCCAAAACTTTAAGCCTGCTCCTGCCACCAACACTCAGAATTATGCTACATAC
    2641 ------------+----------+----------+----------+----------+----------+ 2700
         TTCTTGTGGGTTTTGAAATTCGGACGAGGACGGTGGTTGTGAGTCTTAATACGATGTATG a        K  N  T  Q  N  F  K  P  A  P  A  T  N  T  Q  N  Y  A  T  Y    -

AGAGAAGGCTACAACGTGTATGGAACAGAGAGTGTTAAGATCTAGGGATCCCTTCCCACT
    2701 ------------+----------+----------+----------+----------+----------+ 2760
         TCTCTTCCGATGTTGCACATACCTTGTCTCTCACAATTCTAGATCCCTAGGGAAGGGTGA a        R  E  G  Y  N  V  Y  G  T  E  S  V  K  I  *                    -

GGAGGCATGTGATGAGAGGAAATCACCGAAAACGTGGCTGCTTCAAGGATCCTGAGCCAG
    2761 ------------+----------+----------+----------+----------+----------+ 2820
         CCTCCGTACACTACTCTCCTTTAGTGGCTTTTGCACCGACGAAGTTCCTAGGACTCGGTC
```

FIG. 3F

```
       ATTTCACTCTCCTTGGTGTCGGGCATGACACGAATATTGCTGATGGTGCAATGACCTTTC
2821   ---------+---------+---------+---------+---------+---------+ 2880
       TAAAGTGAGAGGAACCACAGCCCGTACTGTGCTTATAACGACTACCACGTTACTGGAAAG

AATAGGAAAAACTGATTTTTTTTTCCTTCAGTGCCTTATGGAACACTCTGAGACTCGCG
2881   ---------+---------+---------+---------+---------+---------+ 2940
       TTATCCTTTTTGACTAAAAAAAAAGGAAGTCACGGAATACCTTGTGAGACTCTGAGCGC

ACAATGCAAACCATCATTGAAATCTTTTTGCTTTGCTTGAAAAAAAATAATTAAAATAAA
2941   ---------+---------+---------+---------+---------+---------+ 3000
       TGTTACGTTTGGTAGTAACTTTAGAAAAACGAAACGAACTTTTTTTTATTAATTTTATTT

AACCAACAAAAATGGACATGCATCAAACCCTTGATGTATTAATATTTATTATAGTTTTCA
3001   ---------+---------+---------+---------+---------+---------+ 3060
       TTGGTTGTTTTTACCTGTACGTAGTTTGGGAACTACATAATTATAAATAATATCAAAAGT

TTAGGAATTC
3061   ---------+ 3070
       AATCCTTAAG
```

FIG. 6

```
GluR3A    ..GSALGNAVNLAVLKLNEQGLLDKLKNKWWYDKGECGSGGGDSKDKT..
            IIIIII   III IIIIIIII III IIIIIIIIIIIII   IIIIII
GluR3B    ..GSALGTPVNLAVLKLSEQGILDKLKNKWWYDKGECGAKDSGSKDKT..
```

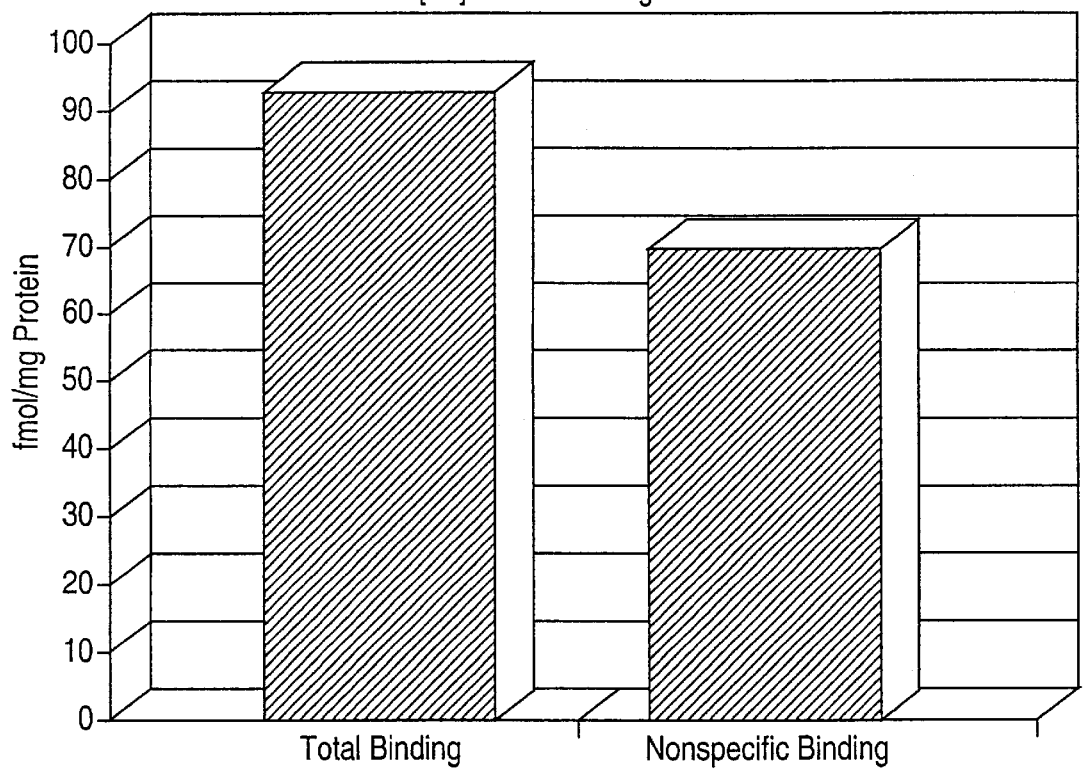

AMPA-BINDING HUMAN GLUR3 RECEPTORS

This application is a division, of application Ser. No. 07/896,612, filed Jun. 10, 1992, now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impluses is controlled by the interaction between a neurotransmitter substance released by the "sending" neuron which then binds to a surface receptor on the "receiving" neuron to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Very recently, genes encoding substituent polypeptides of EAA receptor s from non-human sources, principally rat, have been discovered. Hollmann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettler et al., Neuron 5: 583. 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gene. These authors, as well as Monyer et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et a., Science 252: 851, 1991; Verdoorn et al., Science 252: 1715, 1991; and see WO 91/06648).

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

SUMMARY OF THE INVENTION

The present invention provides a family of isolated polynucleotides that code for AMPA-binding human EAA receptors. By providing polynucleotides that code specifically for CNS receptors native to humans, the present invention provides means for evaluating the human nervous system, and particularly for assessing potentially therapeutic interactions between the AMPA-binding human EAA receptors and selected natural and synthetic ligands.

In one of its aspects, the present invention provides an isolated polynucleotide comprising nucleic acids arranged in a sequence that codes for an EAA receptor belonging to the human GluR3 family. Alternatively, the polynucleotide may code for an AMPA-binding fragment of a human GluR3 receptor, or for an AMPA-binding variant of a human GluR3 receptor. According to one embodiment of the present invention, the isolated polynucleotide encodes a receptor comprising amino acids, arranged in the sequence herein specified with reference to FIGS. 1A–1E (SEQ ID NOS: 1 and 2) and referred to as the human GluR3A receptor. According to another embodiment of the invention, the polynucleotide encodes a variant of the human GluR3A receptor, which variant has the amino acid sequence herein specified with reference to FIGS. 3A–3F (SEQ ID NOS: 3 and 4) and is herein referred to as the human GluR3B receptor. In various specific embodiments of the present invention, the polynucleotide consists of DNA e.g. cDNA, or of RNA e.g. messenger RNA. In other embodiments of the present invention, the polynucleotide may be coupled to a reporter molecule, such as a radioactive label, for use in autoradiographic studies of human GluR3 receptor tissue distribution. In further embodiments of the present invention, fragments of the polynucleotides of the invention, including radiolabelled versions thereof, may be employed either as probes for detection of glutamate receptor-encoding polynucleotides, as primers appropriate for amplifying such polynucleotides present in a biological specimen, or as templates for expression of a GluR3 receptor or an AMPA-binding fragments or variant thereof.

According to another aspect of the present invention, there is provided a cellular host having incorporated therein a polynucleotide of the present invention. In embodiments of the present invention, the polynucleotide is a DNA molecule and is incorporated for expression and secretion in the cellular host, to yield a functional, membrane-bound human GluR3 receptor. In other embodiments of the present invention, the polynucleotide is an RNA molecule which is incorporated in the cellular host to yield the human GluR3 receptor as a functional, membrane-bound product of translation.

According to another aspect of the invention, there is provided a process for obtaining a substantially homogeneous source of a human EAA receptor useful for performing ligand binding assays, which comprises the steps of culturing a genetically engineered cellular host of the invention, and then recovering the cultured cells. Optionally, the cultured cells may be treated to obtain membrane preparations thereof, for use in the ligand binding assays.

According to another aspect of the present invention, there is provided a method for assaying interaction between a test ligand and a human EAA receptor, comprising the steps of incubating the test ligand under appropriate conditions with a human GluR3 receptor source, i.e., a cellular host of the invention or a membrane preparation derived therefrom, and then determining between the substance and the receptor source.

These and other aspects of the invention are now described in greater detail with reference to the accompanying drawings, in which:

BRIEF REFERENCE TO THE DRAWINGS

FIGS. 1A–1E provide a DNA sequence (SEQ ID NO: 1) coding for the human GluR3A receptor, and the amino acid (SEQ ID NO: 2) sequence thereof;

FIG. 2 depicts the strategy employed in cloning the human GluR3A receptor-encoding DNA illustrated in FIGS. 1A–1E;

FIGS. 3A–3F provide a DNA sequence (SEQ ID NO: 3) coding for the human GluR3B receptor, and the amino acid (SEQ ID NO: 4) sequence thereof;

Figure 2:
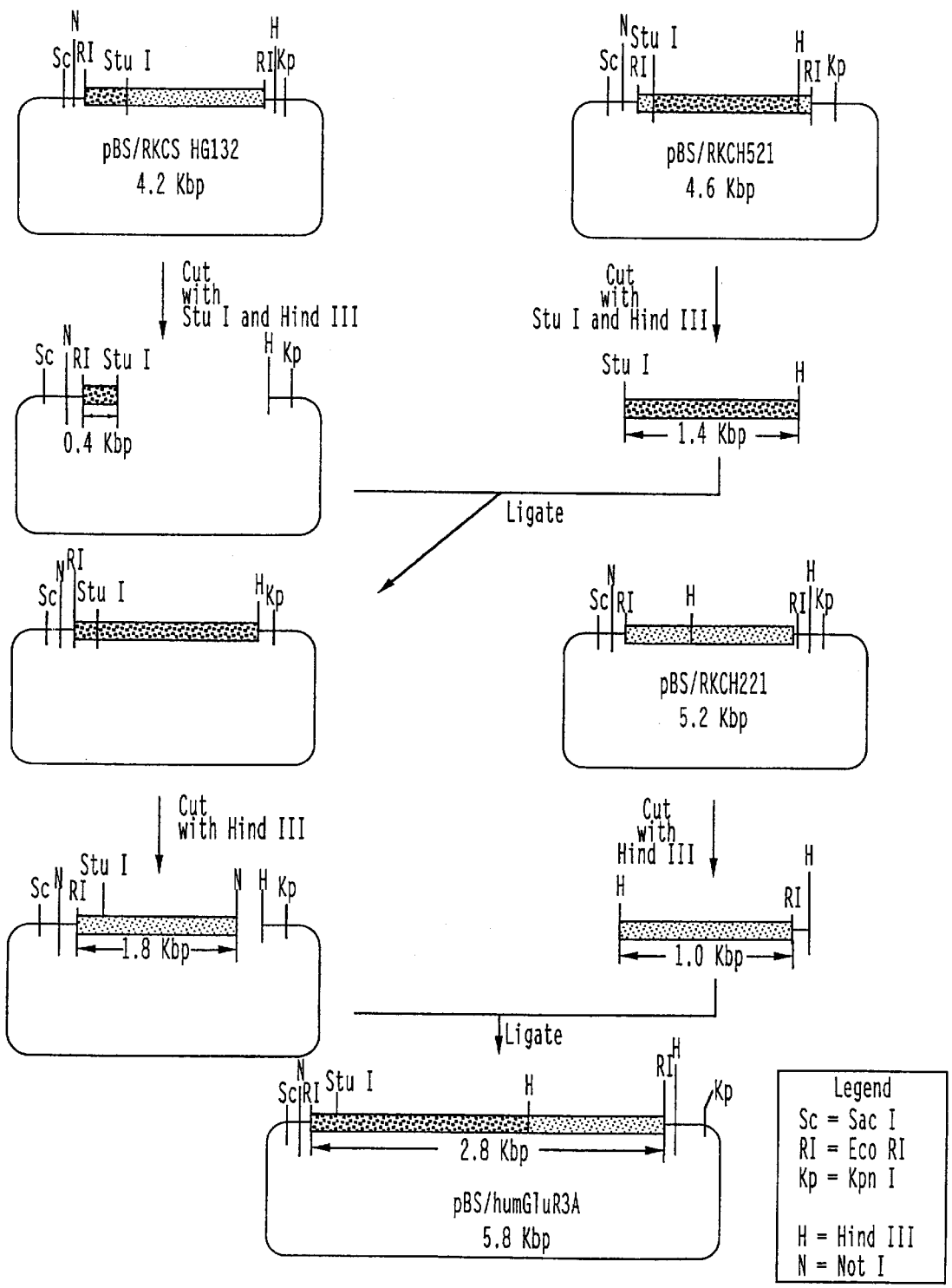

FIG. 6 provides the amino acid sequence of the human GluR3A receptor (SEQ ID NO: 5) and the human GluR3B receptor (SEQ ID NO: 7) in a region of dissimilarity; and FIG. 7 illustrates the AMPA-binding property of the human GluR3A receptor.

DETAILED DESCRIPTION OF THE INVENTION AND ITS PREFERRED EMBODIMENTS

The invention relates to human CNS receptors of the AMPA-binding type, and provides isolated polynucleotides that code for such receptors. The term "isolated" is used herein with reference to intact polynucleotides that are generally less than about 4,000 nucleotides in length and which are otherwise isolated from DNA coding for other human proteins.

In the present context, human CNS receptors of the AMPA-binding type exhibit a characteristic ligand binding profile, which reveals glutamate binding and relative greater affinity for binding AMPA than for other binding other CNS receptor ligands such as kainate, glutamate and their closely related analogues.

In the present specification, an AMPA-binding receptor is said to be "functional" if a cellular host producing it exhibits de novo channel activity when exposed appropriately to AMPA, as determined by the established electrophysiological assays described for example by Hollman et al, supra, or by any other assay appropriate for detecting conductance across a cell membrane.

Members of the human GluR3 family of the invention possess structural features characteristic of the EAA receptors in general, including extracellular N- and C-terminal regions, as well as four internal hydrophobic domains which serve to anchor the receptor within the cell surface membrane. The GluR3A member of the human GluR3 family is a protein characterized structurally as a single polypeptide chain that is produced initially in precursor form bearing a 22 amino acid residue N-terminal signal peptide, and is transported to the cell surface in mature form, lacking the signal peptide and consisting of 866 amino acids arranged in the sequence illustrated, by single letter code, in FIGS. 1A–1E and SEQ ID NO: 2. Unless otherwise stated, the term human GluR3A receptor refers to the mature form of the receptor, and amino acid residues of the individual human GluR3 receptors are accordingly numbered with reference to the mature protein sequence. With respect to structural domains of the receptor, hydropathy analysis reveals four putative transmembrane domains, one spanning residues 527–546 inclusive (TM-1), another spanning residues 575–593 (TM-2), a third spanning residues 604–622 (TM-3) and the fourth spanning residues 796–816 (TM-4). Based on this assignment, it is likely that the human GluR3A receptor structure, in its natural membrane-bound form, consists of a 526 amino acid N-terminal extracellular domain, followed by a hydrophobic region containing four transmembrane domains and an extracellular, 50 amino acid C-terminal domain.

As shown in FIGS. 3A–3F and SEQ ID NOS: 3 and 4, a structurally related variant of the human GluR3A receptor that occurs naturally in human brain tissue has also been identified, and is designated herein as the human GluR3B receptor. Like GluR3A, the GluR3B receptor is also 866 amino acids in length in its mature, membrane-bound form, and initially bears a signal peptide identical to that borne on the GluR3A receptor. Four transmembrane domains are also apparent from the GluR3B sequence, and indicate that these domains lie in the same amino acid regions just indicated in connection with the GluR3A receptor.

With respect to primary structure, the human GluR3B receptor differs from the GluR3A receptor in a 36 amino acid region separating transmembrane domains TM-3 and TM-4, i.e. residues 748–783. For comparison, the sequences of GluR3A and GluR3B in this region are compared in FIG. 6 and are also show in SEQ ID NOS: 5 and 6.

Binding assays performed with various ligands, and with membrane preparations derived from mammalian cells engineered genetically to produce the human GluR3 receptors in membrane-bound form indicate that both human GluR3A and human GluR3B bind selectively to AMPA, relative particularly to kainate and NMDA. This feature, coupled with the medically significant connection between AMPA-type receptors and neurological disorders and disease indicate that the present receptors, as well as AMPA-binding fragments and variants thereof, will serve as valuable tools in the screening and discovery of ligands useful to modulate in vivo interactions between such receptors and their natural ligand, glutamate. Thus, a key aspect of the present invention resides in the construction of cells that are engineered genetically to produce human GluR3 receptor, to serve as a ready and homogeneous source of receptor for use in in vitro ligand binding and/or channel activation assays.

For use in the ligand binding assays, it is desirable to construct by application of genetic engineering techniques a mammalian cell that produces a human GluR3 receptor as a heterologous and membrane-bound product. According to one embodiment of the invention, the construction of such engineered cells is achieved by introducing into a selected host cell a recombinant DNA construct in which DNA coding for a secretable form of the desired human GluR3 receptor, i.e., a form bearing its native signal peptide or a functional, heterologous equivalent thereof, is linked operably with expression controlling elements that are functional in the selected host to drive expression of the receptor-encoding DNA, and thus elaborate the desired human GluR3 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human GluR3 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevetheless serve as expression hosts, provided that "background" binding to the test ligand is accounted for in the assay results.

According to one embodiment of the present invention, the cell line selected to serve as host for human GluR3 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the human GluR3 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for a secretable form of the receptor is linked with expression controlling DNA sequences recognized by the host, and which include a region 5' of the receptor-encoding DNA to drive expression, and a 3' region to terminate expression. The plasmidic vector harbouring the recombinant DNA expression construct typically incorporates such other functional components as an origin of replication, usually virally-derived, to permit replication of the plasmid in the expression host and desirably also for plasmid amplification in a bacterial host, such as *E. coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e. the metalothionein gene promoter, and other steroid-inducible promoters.

For incorporation into the recombinant DNA expression vector, DNA coding for a selected human GluR3 receptor, e.g. the human GluR3A receptor, the human GluR3B receptor or an AMPA-binding fragment or variant thereof, can be obtained by applying selected techniques of gene isolation or gene synthesis. As described in more detail in the examples herein, the human GluR3A receptor and the human GluR3B receptor are encoded within the genome of human brain tissue, and can therefore be obtained from human DNA libraries by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in for example a bacterial plasmid, more typically a bacteriophage. Such bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

In a specific embodiment of the invention, the selected GluR3 receptor is encoded by the DNA sequence illustrated In FIGS. 1A–1E SEQ ID NO: 1, for the GluR3A receptor, and by the DNA sequence illustrated in FIGS. 3A–3F, SEQ ID NO: 3for the GluR3B receptor. In an obvious alternative, the DNA sequences coding for the selected receptor may be a synonymous codon equivalent of the illustrated DNA sequences.

The illustrated DNA sequences constitute cDNA sequences identified in human brain cDNA libraries in the manner exemplified herein. Having herein provided the nucleotide sequence of various members of the human GluR3 receptor family, however, it will be appreciated that polynucleotides encoding the receptors can be obtained by other routes. Automated techniques of gene synthesis and/or amplification can be performed to generate DNA coding therefor. Because of the length of the human GluR3 receptor-encoding DNA, application of automated synthesis may require staged gene construction, in which regions of the gene up to about 300 nucleotides in length are synthesized individually and then ligated in correct succession by overhang complementarity for final assembly. Individually synthesized gene regions can be amplified prior to assembly, using established polymerase chain reaction (PCR) technology.

The application of automated gene synthesis techniques provides an opportunity for generating polynucleotides that encode variants of naturally occurring human GluR3A and GluR3B receptors. It will be appreciated, for example, that polynucleotides coding for the human GluR3 receptors herein described can be generated by substituting synonymous codons for those represented in the naturally occurring polynucleotide sequences herein identified. In addition, polynucleotides coding for human GluR3 receptor variants can be generated which for example incorporate one or more e.g. 1–10, single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the *E. coli* gpt gene which confers resistance to mycophenolic acid, the neo gene from transposon Tn5 which confers resistance to the antibiotic G418 and to neomycin, the dhfr sequence from murine cells or *E. coli* which changes the phenotype of DHFR– cells into DHFR+ cells, and the tk gene of herpes simplex virus, which makes TK– cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a substance, i.e., a candidate ligand, to a human GluR3 receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to AMPA. This competitive binding assay can be performed by incubating the membrane preparation with radiolabelled AMPA, for example [3H]-AMPA, in the presence of unlabelled test compound added at varying concentrations. Following incubation, either displaced or bound radiolabelled AMPA can be recovered and measured, to determine the relative binding affinities of the test compound and AMPA for the particular receptor used as substrate. In this way, the affinities of various compounds for the AMPA-binding human EAA receptors can be measured. Alternatively, a radiolabelled analogue of glutamate may be employed in place of radiolabelled AMPA, as competing ligand.

As an alternative to using cells that express receptor-encoding DNA, ligand characterization may also be performed using cells for example *Xenopus oocytes*, that yield functional membrane-bound receptor following introduction by injection either of receptor-encoding messenger RNA into the oocyte cytoplasm, or of receptor-encoding DNA into the oocyte nucleus. To generate the messenger RNA of cytoplasmic delivery, the receptor-encoding DNA is typically subcloned first into a plasmidic vector adjacent a suitable promoter region, such as the T3 or T7 bacteriophage promoters, to enable transcription into RNA message. RNA is then transcribed from the inserted gene in vitro, collected and then injected into *Xenopus oocytes*. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell, in the established manner.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the human GluR3 receptor responsible for AMPA-binding resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length human GluR receptor-encoding DNA may be modified by site-directed mutagenesis, so as to introduce a translational stop codon into the extracellular N-terminal region, immediately before the sequence encoding the first transmembrane domain (TM1), i.e., before residue 527 as shown in FIGS. 1A–1E SEQ ID NOS: 1)and 2. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 817–866 inclusive (FIGS. 1A–1E SEQ ID NO: 1 and 2). In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such AMPA-binding fragments of a GluR3 receptor may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. *Aspergillus nidulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of a human GluR3 receptor, for example in brain tissue, the present invention also provides, in another of its aspects, labelled antibody to a human GluR3 receptor. To raise such antibodies, there may be used as immunogen either the intact, soluble receptor or an immunogenic fragment thereof i.e. a fragment capable of eliciting an immune response, produced in a microbial or mammalian cell host as described above or by standard peptide synthesis techniques. Regions of human GluR3 receptor particularly suitable for use as immunogenic fragments include those corresponding in sequence to an extracellular region of the receptor, or a portion of the extracellular region, such as peptides consisting of residues 1–526 or a fragment thereof comprising at least about 10 residues, including particularly fragments containing residues 178–193 or 479–522; and peptides corresponding to the region between transmembrane domains TM-2 and TM-3, such as a peptide consisting of residues 594–603. Peptides consisting of the C-terminal domain (residues 817–866), or fragment thereof, may also be used for the raising of antibodies.

The raising of antibodies to the selected human GluR3 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells.

The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for a human GluR3 receptor, and selected regions thereof, may also be used, in accordance with another aspect of the present invention, as hybridization probes for example to identify sequence-related genes resident in the human or other mammalian genomes (or cDNA libraries) or to locate the human GluR3-encoding DNA in a specimen, such as brain tissue. This can be done using either the intact coding region, or a fragment thereof having radiolabelled e.g. $^{32}$P, nucleotides incorporated therein. To identify the human GluR3-encoding DNA in a specimen, it is desirable to use either the full length cDNA coding therefor, or fragment which is unique thereto. With reference to FIGS. 1A–1E and 3A–3F, SEQ ID NOS: 1–4such nucoleotide fragments include those comprising at least about 17 nucleic acids, and otherwise corresponding in sequence to a region coding for an extracellular N-terminal or C-terminal region of the receptor, or representing a 5'-untranslated or 3'-untranslated region thereof. Such oligonucleotide sequences, and the intact gene itself, may also be used of course to clone human GluR3-related human genes, particularly cDNA equivalents thereof, by standard hybridization techniques.

EXAMPLE 1

Isolation of DNA Coding for the Human GluR3A Receptor

The particular strategy used to clone the human GluR3A receptor is depicted schematically in FIG. 2, and described in greater detail below.

cDNA coding for the human GluR3A receptor was identified by probing human hippocampal cDNA that was obtained as an EcoRI-based lambda phage library (lambda ZAP) from Stratagene Cloning Systems (La Jolla, Calif., U.S.A.). The cDNA library was probed initially with a 1.1 kb EcoRI/EcoRI DNA fragment constituting the 3' region of a kainate-binding human EAA receptor, designated humEAA 1a. This particular kainate-binding receptor is described in our co-pending U.S. patent application Ser. No. 07/750,090 filed Aug. 26, 1991 and incorporated herein by reference. DNA coding for the human EAA 1a receptor, and from which the 1.1 kb probe may be recovered, was deposited under terms of the Budapest Treaty, with the American Type Culture Collection in Rockville, Md. U.S.A. on Aug. 21, 1991 under accession number ATCC 75063.

Hybridizations using the probe were carried out at 30 C overnight, and filters were washed with 2×SSC containing 0.5% SDS at 25 C for 5 minutes, followed by a 15 minute wash at 50 C with 2×SSC containing 0.5% SDS. The final wash was with 1×SSC containing 0.5% SDS at 50 C for 15 minutes. Filters were exposed to X-ray film (Kodak) overnight. Of $10^6$ clones screened under the following hybridization conditions (6×SSC, 50% formamide, 5% Denhardt's solution, 0.5% SDS, 100 ug/ml denatured salmon sperm DNA), only two hippocampal cDNA library inserts were identified, one about 1.6 kb and designated RKCH521 and another about 2.2 kb and designated RKCH221 (FIG. 2). For sequencing, the '521 and the '221 phages were plaque purified, then excised as phagemids according to the supplier's specifications, to generate insert-carrying Bluescript-SK variants of the phagemid vector. Sequencing of the '221 clone across its entire sequence revealed a putative ATG initiation codon together with about 78 bases of 5' non-coding region and about 2.1 kb of coding region. Sequencing across the '521 insert revealed a significant region of overlap with the '221 insert, and provided some additional 3' sequence, although no termination codon was located.

There being no termination codon apparent in the '521 sequence, a 3' region of the gene was sought. For this purpose, there was first synthesized an oligonucleotide probe capable, of annealing to the 3' region of the rat GluR3 receptor sequence (SEQ ID NO: 7) reported by Keinanen et al, supra. The specific sequence of the 32-P-labelled probe is provided below:

5'-ACACTCAGAATTACGCTACATACAGAGAAG GCTACAACGT-3'

The same hippocampal cDNA library was then re-screened using the rat-based probe and under the following hybridization conditions; 6×SSC, 25% formamide, 5% Dernhardt's solution, 0.5% SDS, 100 ug/ml denatured salmon sperm DNA, 42 C. This revealed a 1.2 kb insert, designated RKCSHG132. Sequencing of the entire insert revealed 5' overlap with the 3' end of the previously isolated '521 insert, and also revealed a termination codon as well as about 15 bases of 3' non-translated sequence.

To provide the entire coding region in an intact clone, the strategy shown in FIG. 2 was employed, to generate the phagemid pBS/HumGluR3A which carries the hGluR3A-encoding DNA as a 2.8 kb EcoRI/EcoRI insert in a 3.0 kb Bluescript-SK phagemid background. The entire sequence of the EcoRI/EcoRI insert is provided in FIGS. 1A–1E and SEQ ID NO: 1.

The 5.8 kb phagemid pBS/humGluR3A was deposited, under the terms of the Budapest Treaty, with the American Type Culture Collection in Rockville, Md. USA on Mar. 19, 1992, and has been assigned accession number ATCC 75218.

EXAMPLE 2

Isolation of DNA Coding for Human GluR3B Receptor

Figure 4:
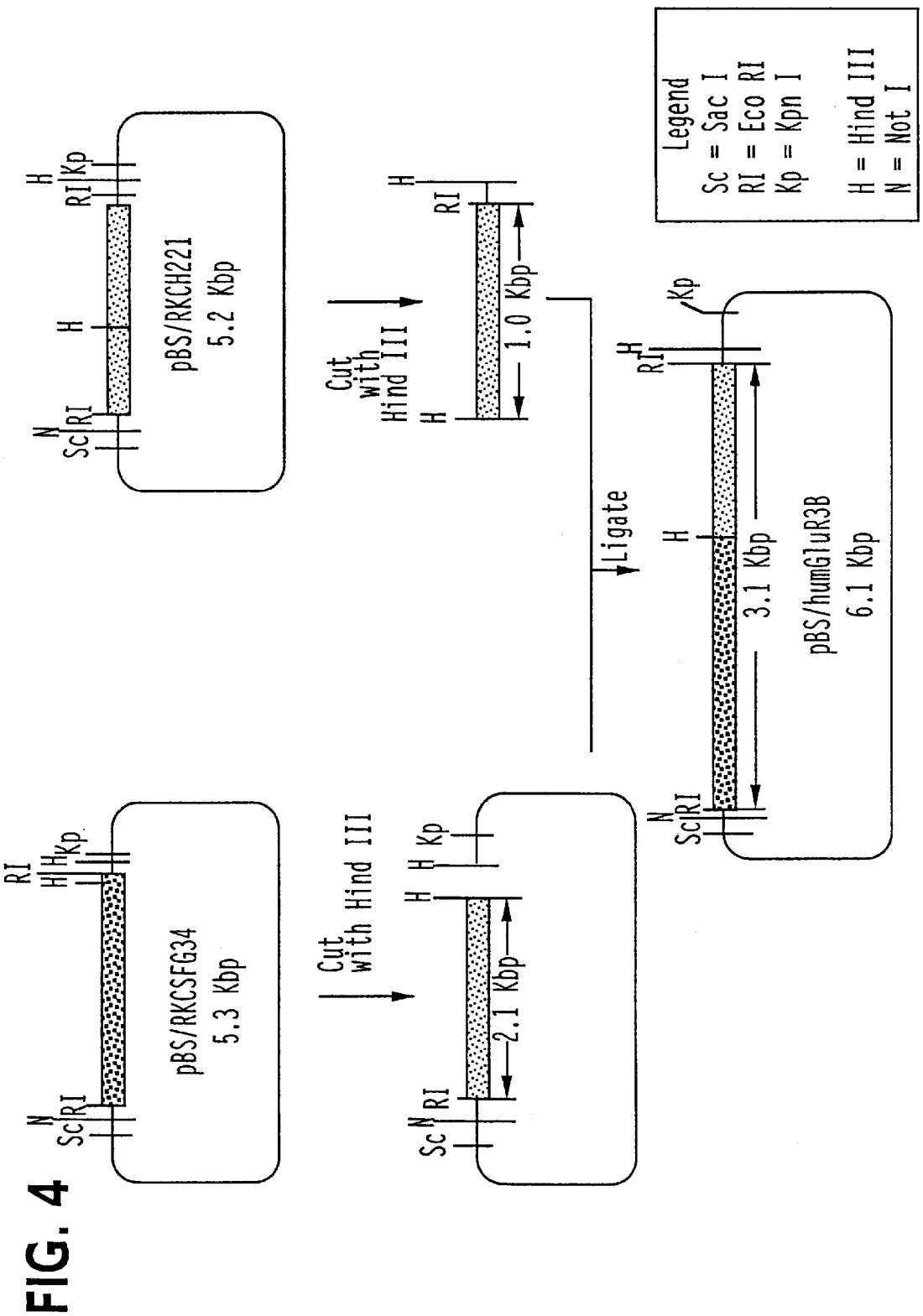
FIG. 4 depicts the strategy employed in cloning the human GluR3B receptor-encoding DNA illustrated in FIGS. 3A–3F.
Figure 5:
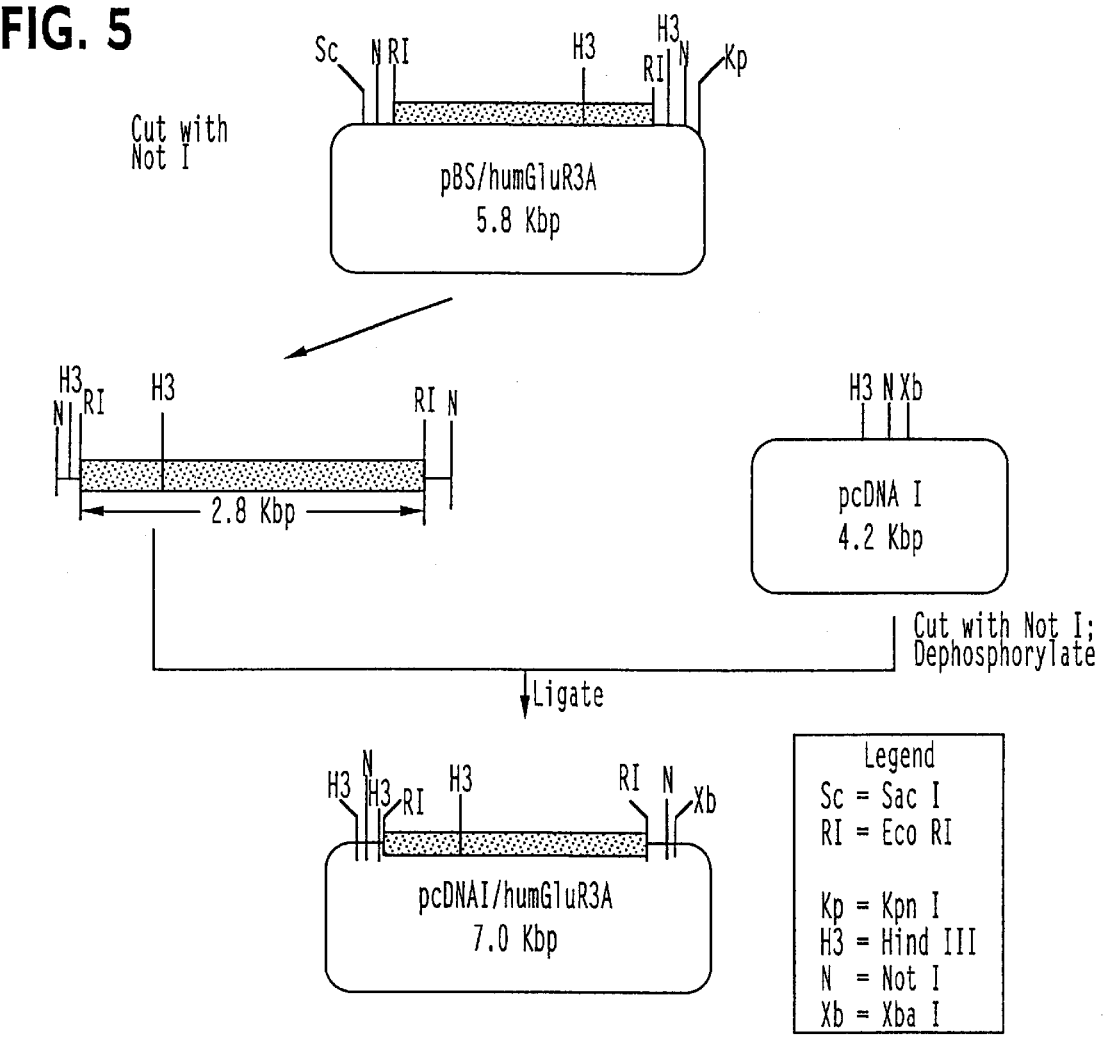
FIG. 5 depicts the strategy employed in generating recombinant DNA expression constructs incorporating the receptor-encoding DNA.

A human fetal brain cDNA library was also screened in the search for human GluR receptors. This particular library was obtained as an EcoRI-based lambda gt 10 library from Strategene Cloning Systems (La Jolla, Calif., U.S.A.). The library was first screened using as hybridization probe an oligonucleotide capable of hybridizing to a 3' region of the reported rat GluR3 gene sequence. Screening using hybridization conditions as noted above (6×SSC, 25% formamide, 42 C, etc.) revealed one insert about 2.3 kb in size, designated RKCSFG34. After excision to release Bluescript-SK phagemids carrying the insert, sequencing revealed substantial sequence identity between the '34 insert and the 3' end of the earlier isolated GluR3A clone, and suggested that the 5' end of the gene encoded on partially on the '34 insert was missing. To provide an assembled gene, a 5' region was excised from the GluR3A insert and used to generate the 5' end of the '34 insert, at an internal HindIII site. This was achieved as depicted schematically in FIG. 4. The resulting intact clone was designated human GluR3B.

Sequence comparison between the GluR3A clone of example 1 and the GluR3B clone of this example revealed only a short region of dissimilarity which is illustrated, in terms of amino acid sequence, in FIG. 6 (the sequences are also shown in (SEQ ID NOS: 5 and 6).

The 6.1 kb phagemid pBS/humGluR3B was deposited, under the terms of the Budapest Treaty, with the American Type Culture Collection in Rockville, Md. USA on Mar. 19, 1992, and has been assigned accession number ATCC 75219.

EXAMPLE 3

Construction of Genetically Engineered Cells Producing Human GluR3 Receptor

For transient expression in mammalian cells, cDNA coding for the human GluR3A receptor was incorporated into the mammalian expression vector pcDNAI, which is available commercially from Invitrogen Corporation (San Diego, Calif., USA; catalogue number V490-20). This is a multifunctional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

To facilitate incorporation of the GluR3A receptor-encoding cDNA into an expression vector, a NotI site was introduced onto the 5' flank of the Bluescript-SK cDNA insert, and the cDNA insert was then released from pBS/humGluR3A as a 2.8 kb NotI/NotI fragment, which was then incorporated at the NotI site in the pcDNAI polylinker. Sequencing across the NotI junction was performed, to confirm proper insert orientation in pcDNAI. The resulting plasmid, designated pcDNAI/humGluR3A, was then introduced for transient expression into a selected mammalian cell host, in this case the monkey-derived, fibroblast like cells of the COS-1 lineage (available from the American Type Culture Collection, Rockville, Md. as ATCC CRL 1650).

For transient expression of the GluR3A-encoding DNA, COS-1 cells were transfected with approximately 8 ug DNA (as pcDNA1/humGluR3A) per $10^6$ COS cells, by DEAE-mediated DNA transfection and treated with chloroquine according to the procedures described by Maniatis et al, supra. Briefly, COS-1 cells were plated at a density of $5\times10^6$ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 uM chloroquine, 10% NuSerum, DNA (0.4 mg/ml) in DMEM/F12 medium. After incubation for 3 hours at 37 C, cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also prepared using two different cell types as host: CHO K1 and CHO Pro5. To construct these cell lines, cDNA coding for human GluR3A was incorporated into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5\times10^5$ in 10% FBS-supplemented MEM medium. After growth for 24 hours, fresh medium are added to the plates and three hours later, the cells are transfected using the calcium phosphate-DNA co-precipitation procedure (Maniatis et al, supra). Briefly, 3 ug of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 4

Ligand Binding Assays

Transfected cells in the frozen state were resuspended in ice-cold distilled water using a hand homogenizer, sonicated for 5 seconds, and then centrifuged for 20 minutes at 50,000 g. The supernatant was discarded and the membrane pellet stored frozen at −70 C.

COS cell membrane pellets were suspended in ice cold 50 mM Tris-HCl (pH 7.55, 5 C) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation was used as tissue source for binding experiments described below. Proteins were determined using the Pierce Reagent with BSA as standard.

Binding assays were then performed, using an amount of COS-derived membrane equivalent to from 25–100 ug as judged by protein determination and selected radiolabelled ligand. In particular, for AMPA-binding assays, incubation mixtures consisted of 25–100 ug tissue protein and D,L-alpha-[5-methyl-3H]amino-3-hydroxy-5-methylisoxazole-4-propionic acid (3H-AMPA, 27.6 Ci/mmole, 10 nM final) with 0.1M KSCN and 2.5 mM $CaCl_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 6 ml of the cold incubation buffer, then 5 ml of Beckman Ready-Protein Plus scintillation cocktail was added, for counting.

For kainate-binding assays, incubation mixtures consisted of 25–100 ug tissue protein and [vinylidene-3H] kainic acid (58 Ci/mmole, 5 nM final) in the cold incubation buffer, 1 ml final volume. Non-specific binding was determined in the presence of 1 mM L-glutamate. Samples were incubated as for the AMPA-binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Protein Plus scintillation cocktail for counting.

Assays performed in this manner, using membrane preparations derived from the human GluR3A receptor-producing COS cells, revealed specific binding of 25–30 fmole/mg protein, at 10 nM [3H]-AMPA (FIG. 7). Mock transfected cells exhibited no specific binding of any of the ligands tested. These results demonstrate clearly that the human GluR3 receptor is binding AMPA with specificity. This activity, coupled with the fact that there is little or no demonstrable binding of either kainate or NMDA, clearly assigns the human GluR3 receptor to be of the AMPA type of EAA receptor. Furthermore, this binding profile indicates that the receptor is binding in an authentic manner, and can therefore reliably predict the ligand binding "signature" of its non-recombinant counterpart from the human brain. These features make the recombinant receptor especially useful for selecting and characterizing ligand compounds which bind to the receptor, and/or for selecting and characterizing compounds which may act by displacing other ligands from the receptor. The isolation of the GluR3 receptor genes in substantially pure form, capable of being expressed as a single, homogeneous receptor species, therefore frees the ligand binding assay from the lack of precision introduced when complex, heterogeneous receptor preparations from human and other mammalian brains are used to attempt such characterizations.

We claim:

1. A method of assaying a substance for binding to human GluR3, which comprises the steps of:
    incubating a cellular host, or a membrane preparation derived from said cellular host, with labelled GluR3 ligand to form a ligand/receptot complex, the cellular host having incorporated expressibly therein a heterologous polynucleotide that encodes a human GluR3 selected from the group consisting of human GluR3A and human GluR3B,
    removing unbound ligand, and
    measuring the amount of ligand displaced from or remaining in the receptor/ligand complex.

2. A method as claimed in claim 1, wherein the cellular host has incorporated expressibly therein a heterologous polynucleotide that encodes human GluR3A having the sequence of SEQ ID NO: 2.

3. A method as claimed in claim 1, wherein the cellular host has incorporated expressibly therein a heterologous polynucleotide that encodes human GluR3B having the sequence of SEQ ID NO: 4.

4. A method as claimed in claim 1, wherein the heterologous polynucleotide is plasmid pBS/humGluR3A (ATCC 75218).

5. A method as claimed in claim 1, wherein the heterologous polynucleotide is plasmid pBS/humGluR3B (ATCC 75219).

6. A method according to claim 1, wherein the cellular host is a mammalian cell.

7. A method according to claim 1, wherein the cellular host is an oocyte.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 2761 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig_ peptide
        (B) LOCATION: 79..144

(ix) FEATURE:
        (A) NAME/KEY: mat_ peptide
        (B) LOCATION: 145..2745

(ix) FEATURE:
        (A) NAME/KEY: CDS
        (B) LOCATION: 79..2745

(xi) SEQUENCE DESCRIPTION: SEQ ID NO:1:

```
GAATTCCTGA CGACTCCTGA GTTGCGCCCA TGCTCTTGTC AGCTTCGTTT T AGGCGTAGC          60

ATGGCCAGGC AGAAGAAA ATG GGG CAA AGC GTG CTC CGG  GCG GTC TTC TTT          111
                    Met Gly Gln Ser Val Leu Arg Ala Val Phe Phe
                    -22     -20                 -15

TTA GTC CTG GGG CTT TTG GGT CAT TCT CAC G GA GGA TTC CCC AAC ACC          159
Leu Val Leu Gly Leu Leu Gly His Ser His G ly Gly Phe Pro Asn Thr
    -10                 -5                   1                 5

ATC AGC ATA GGT GGA CTT TTC ATG AGA AAC A CA GTG CAG GAG CAC AGC          207
Ile Ser Ile Gly Gly Leu Phe Met Arg Asn T hr Val Gln Glu His Ser
                10                  15                  20

GCT TTC CGC TTT GCC GTG CAG TTA TAC AAC A CC AAC CAG AAC ACC ACC          255
Ala Phe Arg Phe Ala Val Gln Leu Tyr Asn T hr Asn Gln Asn Thr Thr
            25                  30                  35

GAG AAG CCC TTC CAT TTG AAT TAC CAC GTA G AT CAC TTG GAT TCC TCC          303
Glu Lys Pro Phe His Leu Asn Tyr His Val A sp His Leu Asp Ser Ser
        40                  45                  50

AAT AGT TTT TCC GTG ACA AAT GCT TTC TGC T CC CAG TTC TCG AGA GGG          351
Asn Ser Phe Ser Val Thr Asn Ala Phe Cys S er Gln Phe Ser Arg Gly
    55                  60                  65

GTG TAT GCC ATC TTT GGA TTC TAT GAC CAG A TG TCA ATG AAC ACC CTG          399
Val Tyr Ala Ile Phe Gly Phe Tyr Asp Gln M et Ser Met Asn Thr Leu
70                  75                  80                  85

ACC TCC TTC TGT GGG GCC CTG CAC ACA TCC T TT GTT ACG CCT AGC TTC          447
Thr Ser Phe Cys Gly Ala Leu His Thr Ser P he Val Thr Pro Ser Phe
                90                  95                  100

CCC ACT GAC GCA GAT GTG CAG TTT GTC ATC C AG ATG CGC CCA GCC TTG          495
```

-continued

```
Pro Thr Asp Ala Asp Val Gln Phe Val Ile Gln Met Arg Pro Ala Leu
        105                 110                 115

AAG GGC GCT ATT CTG AGT CTT CTG GGT CAT TAC AAG TGG GAG AAG TTT          543
Lys Gly Ala Ile Leu Ser Leu Leu Gly His Tyr Lys Trp Glu Lys Phe
        120                 125                 130

GTG TAC CTC TAT GAC ACA GAA CGA GGA TTT TCC ATC CTC CAA GCG ATT          591
Val Tyr Leu Tyr Asp Thr Glu Arg Gly Phe Ser Ile Leu Gln Ala Ile
        135                 140                 145

ATG GAA GCA GCA GTG CAA AAC AAC TGG CAA GTA ACA GCA AGG TCT GTG          639
Met Glu Ala Ala Val Gln Asn Asn Trp Gln Val Thr Ala Arg Ser Val
150                 155                 160                 165

GGA AAC ATA AAG GAC GTC CAA GAA TTC AGG CGC ATC ATT GAA GAA ATG          687
Gly Asn Ile Lys Asp Val Gln Glu Phe Arg Arg Ile Ile Glu Glu Met
                170                 175                 180

GAC AGG AGG CAG GAA AAG CGA TAC TTG ATT GAC TGC GAA GTC GAA AGG          735
Asp Arg Arg Gln Glu Lys Arg Tyr Leu Ile Asp Cys Glu Val Glu Arg
                185                 190                 195

ATT AAC ACA ATT TTG GAA CAG GTT GTG ATC CTA GGG AAA CAC TCA AGA          783
Ile Asn Thr Ile Leu Glu Gln Val Val Ile Leu Gly Lys His Ser Arg
                200                 205                 210

GGT TAT CAC TAC ATG CTC GCT AAC CTG GGT TTT ACT GAT ATT TTA CTG          831
Gly Tyr His Tyr Met Leu Ala Asn Leu Gly Phe Thr Asp Ile Leu Leu
        215                 220                 225

GAA AGA GTC ATG CAT GGG GGA GCC AAC ATT ACA GGT TTC CAG ATT GTC          879
Glu Arg Val Met His Gly Gly Ala Asn Ile Thr Gly Phe Gln Ile Val
230                 235                 240                 245

AAC AAT GAA AAC CCT ATG GTT CAG CAG TTC ATA CAG CGC TGG GTG AGG          927
Asn Asn Glu Asn Pro Met Val Gln Gln Phe Ile Gln Arg Trp Val Arg
                250                 255                 260

CTG GAT GAA AGG GAA TTC CCT GAA GCC AAG AAT GCA CCA CTA AAG TAT          975
Leu Asp Glu Arg Glu Phe Pro Glu Ala Lys Asn Ala Pro Leu Lys Tyr
                265                 270                 275

ACA TCT GCA TTG ACA CAC GAC GCA ATA CTG GTC ATA GCA GAA GCT TTC         1023
Thr Ser Ala Leu Thr His Asp Ala Ile Leu Val Ile Ala Glu Ala Phe
                280                 285                 290

CGC TAC CTG AGG AGG CAG CGA GTA GAT GTG TCC CGG AGA GGA AGT GCT         1071
Arg Tyr Leu Arg Arg Gln Arg Val Asp Val Ser Arg Arg Gly Ser Ala
        295                 300                 305

GGA GAC TGC TTA GCA AAT CCT GCT GTG CCC TGG AGT CAA GGA ATT GAT         1119
Gly Asp Cys Leu Ala Asn Pro Ala Val Pro Trp Ser Gln Gly Ile Asp
310                 315                 320                 325

ATT GAG AGA GCT CTG AAA ATG GTG CAA GTA CAA GGA ATG ACT GGA AAT         1167
Ile Glu Arg Ala Leu Lys Met Val Gln Val Gln Gly Met Thr Gly Asn
                330                 335                 340

ATT CAA TTT GAC ACT TAT GGA CGT AGG ACA AAT TAT ACC ATC GAT GTG         1215
Ile Gln Phe Asp Thr Tyr Gly Arg Arg Thr Asn Tyr Thr Ile Asp Val
        345                 350                 355

TAT GAA ATG AAA GTC AGT GGC TCT CGA AAA GCT GGC TAC TGG AAC GAG         1263
Tyr Glu Met Lys Val Ser Gly Ser Arg Lys Ala Gly Tyr Trp Asn Glu
        360                 365                 370

TAT GAA AGG TTT GTG CCT TTC TCA GAT CAG CAA ATC AGC AAT GAC AGT         1311
Tyr Glu Arg Phe Val Pro Phe Ser Asp Gln Gln Ile Ser Asn Asp Ser
        375                 380                 385

GCA TCC TCA GAG AAT CGG ACC ATA GTA GTG ACT ACC ATT CTG GAA TCA         1359
Ala Ser Ser Glu Asn Arg Thr Ile Val Val Thr Thr Ile Leu Glu Ser
390                 395                 400                 405

CCA TAT GTA ATG TAC AAG AAG AAC CAT GAG CAA CTG GAA GGA AAT GAA         1407
Pro Tyr Val Met Tyr Lys Lys Asn His Glu Gln Leu Glu Gly Asn Glu
                410                 415                 420
```

```
CGA TAT GAA GGC TAT TGT GTA GAC CTA GCC T AT GAA ATA GCC AAA CAT       1455
Arg Tyr Glu Gly Tyr Cys Val Asp Leu Ala T yr Glu Ile Ala Lys His
            425                 430                 435

GTA AGG ATC AAA TAC AAA TTG TCC ATC GTT G GT GAC GGG AAA TAT GGT       1503
Val Arg Ile Lys Tyr Lys Leu Ser Ile Val G ly Asp Gly Lys Tyr Gly
            440                 445                 450

GCA AGG GAT CCA GAG ACT AAA ATA TGG AAC G GC ATG GTT GGG GAA CTT       1551
Ala Arg Asp Pro Glu Thr Lys Ile Trp Asn G ly Met Val Gly Glu Leu
            455                 460                 465

GTC TAT GGG AGA GCT GAT ATA GCT GTT GCT C CA CTC ACT ATA ACA TTG       1599
Val Tyr Gly Arg Ala Asp Ile Ala Val Ala P ro Leu Thr Ile Thr Leu
470                 475                 480                 485

GTC CGT GAA GAA GTC ATA GAT TTT TCA AAG C CA TTA ATG AGC CTG GGC       1647
Val Arg Glu Glu Val Ile Asp Phe Ser Lys P ro Leu Met Ser Leu Gly
                490                 495                 500

ATC TCC ATC ATG ATA AAG AAG CCT CAG AAA T CA AAA CCA GGC GTA TTC       1695
Ile Ser Ile Met Ile Lys Lys Pro Gln Lys S er Lys Pro Gly Val Phe
                505                 510                 515

TCA TTT CTG GAT CCC CTG GCT TAT GAA ATC T GG ATG TGC ATT GTC TTT       1743
Ser Phe Leu Asp Pro Leu Ala Tyr Glu Ile T rp Met Cys Ile Val Phe
                520                 525                 530

GCT TAC ATT GGA GTC AGC GTA GTT CTT TTC C TA GTC AGC AGG TTC AGT       1791
Ala Tyr Ile Gly Val Ser Val Val Leu Phe L eu Val Ser Arg Phe Ser
                535                 540                 545

CCT TAT GAA TGG CAC TTG GAA GAC AAC AAT G AA GAA CCT CGT GAC CCA       1839
Pro Tyr Glu Trp His Leu Glu Asp Asn Asn G lu Glu Pro Arg Asp Pro
550                 555                 560                 565

CAA AGT CCT CCT GAT CCT CCA AAT GAA TTT G GA ATA TTT AAC AGT CTT       1887
Gln Ser Pro Pro Asp Pro Pro Asn Glu Phe G ly Ile Phe Asn Ser Leu
                570                 575                 580

TGG TTT TCC TTG GGT GCC TTT ATG CAG CAA G GA TGT GAT ATT TCT CCA       1935
Trp Phe Ser Leu Gly Ala Phe Met Gln Gln G ly Cys Asp Ile Ser Pro
                585                 590                 595

AGA TCA CTC TCC GGG CGC ATT GTT GGA GGG G TT TGG TGG TTC TTC ACC       1983
Arg Ser Leu Ser Gly Arg Ile Val Gly Gly V al Trp Trp Phe Phe Thr
                600                 605                 610

CTG ATC ATA ATT TCT TCC TAT ACT GCC AAT C TC GCT GCT TTC CTG ACT       2031
Leu Ile Ile Ile Ser Ser Tyr Thr Ala Asn L eu Ala Ala Phe Leu Thr
                615                 620                 625

GTG GAG AGG ATG GTT TCT CCC ATA GAG AGT G CT GAA GAC TTA GCT AAA       2079
Val Glu Arg Met Val Ser Pro Ile Glu Ser A la Glu Asp Leu Ala Lys
630                 635                 640                 645

CAG ACT GAA ATT GCA TAT GGG ACC CTG GAC T CC GGT TCA ACA AAA GAA       2127
Gln Thr Glu Ile Ala Tyr Gly Thr Leu Asp S er Gly Ser Thr Lys Glu
                650                 655                 660

TTT TTC AGA AGA TCC AAA ATT GCT GTG TAC G AG AAA ATG TGG TCT TAC       2175
Phe Phe Arg Arg Ser Lys Ile Ala Val Tyr G lu Lys Met Trp Ser Tyr
                665                 670                 675

ATG AAA TCA GCG GAG CCA TCT GTG TTT ACC A AA ACA ACA GCA GAC GGA       2223
Met Lys Ser Ala Glu Pro Ser Val Phe Thr L ys Thr Thr Ala Asp Gly
                680                 685                 690

GTG GCC CGA GTG CGA AAG TCC AAG GGA AAG T TC GCC TTC TGC TTG GAG       2271
Val Ala Arg Val Arg Lys Ser Lys Gly Lys P he Ala Phe Leu Leu Glu
695                 700                 705

TCA ACC ATG AAT GAG TAC ATT GAG CAG AGA A AA CCA TGT GAT ACG ATG       2319
Ser Thr Met Asn Glu Tyr Ile Glu Gln Arg L ys Pro Cys Asp Thr Met
710                 715                 720                 725

AAA GTT GGT GGA AAT CTG GAT TCC AAA GGC T AT GGT GTG GCA ACC CCT       2367
Lys Val Gly Gly Asn Leu Asp Ser Lys Gly T yr Gly Val Ala Thr Pro
                730                 735                 740
```

-continued

```
AAA GGC TCA GCA TTA GGA AAT GCT GTT AAC C TG GCA GTA TTA AAA CTG      2415
Lys Gly Ser Ala Leu Gly Asn Ala Val Asn L eu Ala Val Leu Lys Leu
            745                 750                 755

AAT GAG CAA GGC CTC TTG GAC AAA TTG AAA A AC AAA TGG TGG TAC GAC      2463
Asn Glu Gln Gly Leu Leu Asp Lys Leu Lys A sn Lys Trp Trp Tyr Asp
            760                 765                 770

AAA GGA GAG TGC GGC AGC GGG GGC GGT GAC T CC AAG GAC AAG ACC AGC      2511
Lys Gly Glu Cys Gly Ser Gly Gly Gly Asp S er Lys Asp Lys Thr Ser
            775                 780                 785

GCT CTG AGC CTG AGC AAT GTG GCA GGC GTT T TC TAT ATA CTT GTC GGA      2559
Ala Leu Ser Leu Ser Asn Val Ala Gly Val P he Tyr Ile Leu Val Gly
790                 795                 800                 805

GGT CTG GGG CTG GCC ATG ATG GTG GCT TTG A TA GAA TTC TGT TAC AAA      2607
Gly Leu Gly Leu Ala Met Met Val Ala Leu I le Glu Phe Cys Tyr Lys
                810                 815                 820

TCA CGG GCA GAG TCC AAA CGC ATG AAA CTC A CA AAG AAC ACC CAA AAC      2655
Ser Arg Ala Glu Ser Lys Arg Met Lys Leu T hr Lys Asn Thr Gln Asn
            825                 830                 835

TTT AAG CCT GCT CCT GCC ACC AAC ACT CAG A AT TAT GCT ACA TAC AGA      2703
Phe Lys Pro Ala Pro Ala Thr Asn Thr Gln A sn Tyr Ala Thr Tyr Arg
            840                 845                 850

GAA GGC TAC AAC GTG TAT GGA ACA GAG AGT G TT AAG ATC TAGGGATCCC       2752
Glu Gly Tyr Asn Val Tyr Gly Thr Glu Ser V al Lys Ile
855                 860                 865

TTGGAATTC                                                             2761
```

(2) INFORMATION FOR SEQ ID NO:2:

(i) SEQUENCE CHARACTERISTICS:
        (A) LENGTH: 888 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Gln Ser Val Leu Arg Ala Val Phe P he Leu Val Leu Gly Leu
-22         -20                 -15                 -10

Leu Gly His Ser His Gly Gly Phe Pro Asn T hr Ile Ser Ile Gly Gly
     -5                  1                   5                  10

Leu Phe Met Arg Asn Thr Val Gln Glu His S er Ala Phe Arg Phe Ala
                15                  20                  25

Val Gln Leu Tyr Asn Thr Asn Gln Asn Thr T hr Glu Lys Pro Phe His
            30                  35                  40

Leu Asn Tyr His Val Asp His Leu Asp Ser S er Asn Ser Phe Ser Val
            45                  50                  55

Thr Asn Ala Phe Cys Ser Gln Phe Ser Arg G ly Val Tyr Ala Ile Phe
        60                  65                  70

Gly Phe Tyr Asp Gln Met Ser Met Asn Thr L eu Thr Ser Phe Cys Gly
75                  80                  85                  90

Ala Leu His Thr Ser Phe Val Thr Pro Ser P he Pro Thr Asp Ala Asp
                95                  100                 105

Val Gln Phe Val Ile Gln Met Arg Pro Ala L eu Lys Gly Ala Ile Leu
            110                 115                 120

Ser Leu Leu Gly His Tyr Lys Trp Glu Lys P he Val Tyr Leu Tyr Asp
            125                 130                 135

Thr Glu Arg Gly Phe Ser Ile Leu Gln Ala I le Met Glu Ala Ala Val
            140                 145                 150
```

-continued

Gln Asn Asn Trp Gln Val Thr Ala Arg Ser Val Gly Asn Ile Lys Asp
155                 160                 165                 170

Val Gln Glu Phe Arg Arg Ile Ile Glu Glu Met Asp Arg Arg Gln Glu
            175                 180                 185

Lys Arg Tyr Leu Ile Asp Cys Glu Val Glu Arg Ile Asn Thr Ile Leu
            190                 195                 200

Glu Gln Val Val Ile Leu Gly Lys His Ser Arg Gly Tyr His Tyr Met
            205                 210                 215

Leu Ala Asn Leu Gly Phe Thr Asp Ile Leu Leu Glu Arg Val Met His
            220                 225                 230

Gly Gly Ala Asn Ile Thr Gly Phe Gln Ile Val Asn Asn Glu Asn Pro
235                 240                 245                 250

Met Val Gln Gln Phe Ile Gln Arg Trp Val Arg Leu Asp Glu Arg Glu
            255                 260                 265

Phe Pro Glu Ala Lys Asn Ala Pro Leu Lys Tyr Thr Ser Ala Leu Thr
            270                 275                 280

His Asp Ala Ile Leu Val Ile Ala Glu Ala Phe Arg Tyr Leu Arg Arg
            285                 290                 295

Gln Arg Val Asp Val Ser Arg Arg Gly Ser Ala Gly Asp Cys Leu Ala
300                 305                 310

Asn Pro Ala Val Pro Trp Ser Gln Gly Ile Asp Ile Glu Arg Ala Leu
315                 320                 325                 330

Lys Met Val Gln Val Gln Gly Met Thr Gly Asn Ile Gln Phe Asp Thr
            335                 340                 345

Tyr Gly Arg Arg Thr Asn Tyr Thr Ile Asp Val Tyr Glu Met Lys Val
            350                 355                 360

Ser Gly Ser Arg Lys Ala Gly Tyr Trp Asn Glu Tyr Glu Arg Phe Val
            365                 370                 375

Pro Phe Ser Asp Gln Gln Ile Ser Asn Asp Ser Ala Ser Ser Glu Asn
            380                 385                 390

Arg Thr Ile Val Val Thr Thr Ile Leu Glu Ser Pro Tyr Val Met Tyr
395                 400                 405                 410

Lys Lys Asn His Glu Gln Leu Glu Gly Asn Glu Arg Tyr Glu Gly Tyr
            415                 420                 425

Cys Val Asp Leu Ala Tyr Glu Ile Ala Lys His Val Arg Ile Lys Tyr
            430                 435                 440

Lys Leu Ser Ile Val Gly Asp Gly Lys Tyr Gly Ala Arg Asp Pro Glu
            445                 450                 455

Thr Lys Ile Trp Asn Gly Met Val Gly Glu Leu Val Tyr Gly Arg Ala
460                 465                 470

Asp Ile Ala Val Ala Pro Leu Thr Ile Thr Leu Val Arg Glu Glu Val
475                 480                 485                 490

Ile Asp Phe Ser Lys Pro Leu Met Ser Leu Gly Ile Ser Ile Met Ile
            495                 500                 505

Lys Lys Pro Gln Lys Ser Lys Pro Gly Val Phe Ser Phe Leu Asp Pro
            510                 515                 520

Leu Ala Tyr Glu Ile Trp Met Cys Ile Val Phe Ala Tyr Ile Gly Val
            525                 530                 535

Ser Val Val Leu Phe Leu Val Ser Arg Phe Ser Pro Tyr Glu Trp His
            540                 545                 550

Leu Glu Asp Asn Asn Glu Glu Pro Arg Asp Pro Gln Ser Pro Pro Asp
555                 560                 565                 570

```
Pro Pro Asn Glu Phe Gly Ile Phe Asn Ser Leu Trp Phe Ser Leu Gly
                575                 580                 585

Ala Phe Met Gln Gln Gly Cys Asp Ile Ser Pro Arg Ser Leu Ser Gly
                590                 595                 600

Arg Ile Val Gly Gly Val Trp Trp Phe Phe Thr Leu Ile Ile Ile Ser
                605                 610                 615

Ser Tyr Thr Ala Asn Leu Ala Ala Phe Leu Thr Val Glu Arg Met Val
                620                 625                 630

Ser Pro Ile Glu Ser Ala Glu Asp Leu Ala Lys Gln Thr Glu Ile Ala
635                 640                 645                 650

Tyr Gly Thr Leu Asp Ser Gly Ser Thr Lys Glu Phe Phe Arg Arg Ser
                655                 660                 665

Lys Ile Ala Val Tyr Glu Lys Met Trp Ser Tyr Met Lys Ser Ala Glu
                670                 675                 680

Pro Ser Val Phe Thr Lys Thr Thr Ala Asp Gly Val Ala Arg Val Arg
                685                 690                 695

Lys Ser Lys Gly Lys Phe Ala Phe Leu Leu Glu Ser Thr Met Asn Glu
                700                 705                 710

Tyr Ile Glu Gln Arg Lys Pro Cys Asp Thr Met Lys Val Gly Gly Asn
715                 720                 725                 730

Leu Asp Ser Lys Gly Tyr Gly Val Ala Thr Pro Lys Gly Ser Ala Leu
                735                 740                 745

Gly Asn Ala Val Asn Leu Ala Val Leu Lys Leu Asn Glu Gln Gly Leu
                750                 755                 760

Leu Asp Lys Leu Lys Asn Lys Trp Trp Tyr Asp Lys Gly Glu Cys Gly
                765                 770                 775

Ser Gly Gly Gly Asp Ser Lys Asp Lys Thr Ser Ala Leu Ser Leu Ser
                780                 785                 790

Asn Val Ala Gly Val Phe Tyr Ile Leu Val Gly Gly Leu Gly Leu Ala
795                 800                 805                 810

Met Met Val Ala Leu Ile Glu Phe Cys Tyr Lys Ser Arg Ala Glu Ser
                815                 820                 825

Lys Arg Met Lys Leu Thr Lys Asn Thr Gln Asn Phe Lys Pro Ala Pro
                830                 835                 840

Ala Thr Asn Thr Gln Asn Tyr Ala Thr Tyr Arg Glu Gly Tyr Asn Val
                845                 850                 855

Tyr Gly Thr Glu Ser Val Lys Ile
                860                 865

(2) INFORMATION FOR SEQ ID NO:3:

(i) SEQUENCE CHARACTERISTICS:
        (A) LENGTH: 3070 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: sig_ peptide
         (B) LOCATION: 79..144

(ix) FEATURE:
         (A) NAME/KEY: mat_ peptide
         (B) LOCATION: 145..2745

(ix) FEATURE:
         (A) NAME/KEY: CDS
         (B) LOCATION: 79..2745
```

(xi) SEQUENCE DESCRIPTION: SEQ ID NO:3:

```
GAATTCCTGA CGACTCCTGA GTTGCGCCCA TGCTCTTGTC AGCTTCGTTT T AGGCGTAGC      60

ATGGCCAGGC AGAAGAAA ATG GGG CAA AGC GTG CTC CGG  GCG GTC TTC TTT      111
                    Met Gly Gln Ser Val Leu Arg Ala Val Phe Phe
                    -22     -20                 -15

TTA GTC CTG GGG CTT TTG GGT CAT TCT CAC G GA GGA TTC CCC AAC ACC      159
Leu Val Leu Gly Leu Leu Gly His Ser His G ly Gly Phe Pro Asn Thr
        -10             -5                  1                  5

ATC AGC ATA GGT GGA CTT TTC ATG AGA AAC A CA GTG CAG GAG CAC AGC      207
Ile Ser Ile Gly Gly Leu Phe Met Arg Asn T hr Val Gln Glu His Ser
                10                  15                     20

GCT TTC CGC TTT GCC GTG CAG TTA TAC AAC A CC AAC CAG AAC ACC ACC      255
Ala Phe Arg Phe Ala Val Gln Leu Tyr Asn T hr Asn Gln Asn Thr Thr
            25                  30                     35

GAG AAG CCC TTC CAT TTG AAT TAC CAC GTA G AT CAC TTG GAT TCC TCC      303
Glu Lys Pro Phe His Leu Asn Tyr His Val A sp His Leu Asp Ser Ser
        40                  45                     50

AAT AGT TTT TCC GTG ACA AAT GCT TTC TGC T CC CAG TTC TCG AGA GGG      351
Asn Ser Phe Ser Val Thr Asn Ala Phe Cys S er Gln Phe Ser Arg Gly
    55                  60                      65

GTG TAT GCC ATC TTT GGA TTC TAT GAC CAG A TG TCA ATG AAC ACC CTG      399
Val Tyr Ala Ile Phe Gly Phe Tyr Asp Gln M et Ser Met Asn Thr Leu
70              75                      80                  85

ACC TCC TTC TGT GGG GCC CTG CAC ACA TCC T TT GTT ACG CCT AGC TTC      447
Thr Ser Phe Cys Gly Ala Leu His Thr Ser P he Val Thr Pro Ser Phe
                90                  95                 100

CCC ACT GAC GCA GAT GTG CAG TTT GTC ATC C AG ATG CGC CCA GCC TTG      495
Pro Thr Asp Ala Asp Val Gln Phe Val Ile G ln Met Arg Pro Ala Leu
            105                 110                    115

AAG GGC GCT ATT CTG AGT CTT CTG GGT CAT T AC AAG TGG GAG AAG TTT      543
Lys Gly Ala Ile Leu Ser Leu Leu Gly His T yr Lys Trp Glu Lys Phe
        120                 125                    130

GTG TAC CTC TAT GAC ACA GAA CGA GGA TTT T CC ATC CTC CAA GCG ATT      591
Val Tyr Leu Tyr Asp Thr Glu Arg Gly Phe S er Ile Leu Gln Ala Ile
    135                 140                     145

ATG GAA GCA GCA GTG CAA AAC AAC TGG CAA G TA ACA GCA AGG TCT GTG      639
Met Glu Ala Ala Val Gln Asn Asn Trp Gln V al Thr Ala Arg Ser Val
150                 155                     160                165

GGA AAC ATA AAG GAC GTC CAA GAA TTC AGG C GC ATC ATT GAA GAA ATG      687
Gly Asn Ile Lys Asp Val Gln Glu Phe Arg A rg Ile Ile Glu Glu Met
                170                 175                    180

GAC AGG AGG CAG GAA AAG CGA TAC TTG ATT G AC TGC GAA GTC GAA AGG      735
Asp Arg Arg Gln Glu Lys Arg Tyr Leu Ile A sp Cys Glu Val Glu Arg
            185                 190                    195

ATT AAC ACA ATT TTG GAA CAG GTT GTG ATC C TA GGG AAA CAC TCA AGA      783
Ile Asn Thr Ile Leu Glu Gln Val Val Ile L eu Gly Lys His Ser Arg
        200                 205                    210

GGT TAT CAC TAC ATG CTC GCT AAC CTG GGT T TT ACT GAT ATT TTA CTG      831
Gly Tyr His Tyr Met Leu Ala Asn Leu Gly P he Thr Asp Ile Leu Leu
    215                 220                     225

GAA AGA GTC ATG CAT GGG GGA GCC AAC ATT A CA GGT TTC CAG ATT GTC      879
Glu Arg Val Met His Gly Gly Ala Asn Ile T hr Gly Phe Gln Ile Val
230                 235                     240                245

AAC AAT GAA AAC CCT ATG GTT CAG CAG TTC A TA CAG CGC TGG GTG AGG      927
Asn Asn Glu Asn Pro Met Val Gln Gln Phe I le Gln Arg Trp Val Arg
                250                 255                    260

CTG GAT GAA AGG GAA TTC CCT GAA GCC AAG A AT GCA CCA CTA AAG TAT      975
Leu Asp Glu Arg Glu Phe Pro Glu Ala Lys A sn Ala Pro Leu Lys Tyr
```

-continued

```
                  265                 270                 275
ACA TCT GCA TTG ACA CAC GAC GCA ATA CTG G TC ATA GCA GAA GCT TTC        1023
Thr Ser Ala Leu Thr His Asp Ala Ile Leu V al Ile Ala Glu Ala Phe
            280                 285                 290

CGC TAC CTG AGG AGG CAG CGA GTA GAT GTG T CC CGG AGA GGA AGT GCT        1071
Arg Tyr Leu Arg Arg Gln Arg Val Asp Val S er Arg Arg Gly Ser Ala
        295                 300                 305

GGA GAC TGC TTA GCA AAT CCT GCT GTG CCC T GG AGT CAA GGA ATT GAT        1119
Gly Asp Cys Leu Ala Asn Pro Ala Val Pro T rp Ser Gln Gly Ile Asp
310                 315                 320                 325

ATT GAG AGA GCT CTG AAA ATG GTG CAA GTA C AA GGA ATG ACT GGA AAT        1167
Ile Glu Arg Ala Leu Lys Met Val Gln Val G ln Gly Met Thr Gly Asn
                330                 335                 340

ATT CAA TTT GAC ACT TAT GGA CGT AGG ACA A AT TAT ACC ATC GAT GTG        1215
Ile Gln Phe Asp Thr Tyr Gly Arg Arg Thr A sn Tyr Thr Ile Asp Val
            345                 350                 355

TAT GAA ATG AAA GTC AGT GGC TCT CGA AAA G CT GGC TAC TGG AAC GAG        1263
Tyr Glu Met Lys Val Ser Gly Ser Arg Lys A la Gly Tyr Trp Asn Glu
        360                 365                 370

TAT GAA AGG TTT GTG CCT TTC TCA GAT CAG C AA ATC AGC AAT GAC AGT        1311
Tyr Glu Arg Phe Val Pro Phe Ser Asp Gln G ln Ile Ser Asn Asp Ser
    375                 380                 385

GCA TCC TCA GAG AAT CGG ACC ATA GTA GTG A CT ACC ATT CTG GAA TCA        1359
Ala Ser Ser Glu Asn Arg Thr Ile Val Val T hr Thr Ile Leu Glu Ser
390                 395                 400                 405

CCA TAT GTA ATG TAC AAG AAG AAC CAT GAG C AA CTG GAA GGA AAT GAA        1407
Pro Tyr Val Met Tyr Lys Lys Asn His Glu G ln Leu Glu Gly Asn Glu
                410                 415                 420

CGA TAT GAA GGC TAT TGT GTA GAC CTA GCC T AT GAA ATA GCC AAA CAT        1455
Arg Tyr Glu Gly Tyr Cys Val Asp Leu Ala T yr Glu Ile Ala Lys His
            425                 430                 435

GTA AGG ATC AAA TAC AAA TTG TCC ATC GTT G GT GAC GGG AAA TAT GGT        1503
Val Arg Ile Lys Tyr Lys Leu Ser Ile Val G ly Asp Gly Lys Tyr Gly
        440                 445                 450

GCA AGG GAT CCA GAG ACT AAA ATA TGG AAC G GC ATG GTT GGG GAA CTT        1551
Ala Arg Asp Pro Glu Thr Lys Ile Trp Asn G ly Met Val Gly Glu Leu
    455                 460                 465

GTC TAT GGG AGA GCT GAT ATA GCT GTT GCT C CA CTC ACT ATA ACA TTG        1599
Val Tyr Gly Arg Ala Asp Ile Ala Val Ala P ro Leu Thr Ile Thr Leu
470                 475                 480                 485

GTC CGT GAA GAA GTC ATA GAT TTT TCA AAG C CA TTA ATG AGC CTG GGC        1647
Val Arg Glu Glu Val Ile Asp Phe Ser Lys P ro Leu Met Ser Leu Gly
                490                 495                 500

ATC TCC ATC ATG ATA AAG AAG CCT CAG AAA T CA AAA CCA GGC GTA TTC        1695
Ile Ser Ile Met Ile Lys Lys Pro Gln Lys S er Lys Pro Gly Val Phe
            505                 510                 515

TCA TTT CTG GAT CCC CTG GCT TAT GAA ATC T GG ATG TGC ATT GTC TTT        1743
Ser Phe Leu Asp Pro Leu Ala Tyr Glu Ile T rp Met Cys Ile Val Phe
        520                 525                 530

GCT TAC ATT GGA GTC AGC GTA GTT CTT TTC C TA GTC AGC AGG TTC AGT        1791
Ala Tyr Ile Gly Val Ser Val Val Leu Phe L eu Val Ser Arg Phe Ser
    535                 540                 545

CCT TAT GAA TGG CAC TTG GAA GAC AAC AAT G AA GAA CCT CGT GAC CCA        1839
Pro Tyr Glu Trp His Leu Glu Asp Asn Asn G lu Glu Pro Arg Asp Pro
550                 555                 560                 565

CAA AGT CCT CCT GAT CCT CCA AAT GAA TTT G GA ATA TTT AAC AGT CTT        1887
Gln Ser Pro Pro Asp Pro Pro Asn Glu Phe G ly Ile Phe Asn Ser Leu
                570                 575                 580

TGG TTT TCC TTG GGT GCC TTT ATG CAG CAA G GA TGT GAT ATT TCT CCA        1935
```

```
Trp Phe Ser Leu Gly Ala Phe Met Gln Gln G ly Cys Asp Ile Ser Pro
            585                 590                 595

AGA TCA CTC TCC GGG CGC ATT GTT GGA GGG G TT TGG TGG TTC TTC ACC     1983
Arg Ser Leu Ser Gly Arg Ile Val Gly Gly V al Trp Trp Phe Phe Thr
            600                 605                 610

CTG ATC ATA ATT TCT TCC TAT ACT GCC AAT C TC GCT GCT TTC CTG ACT     2031
Leu Ile Ile Ile Ser Ser Tyr Thr Ala Asn L eu Ala Ala Phe Leu Thr
            615                 620                 625

GTG GAG AGG ATG GTT TCT CCC ATA GAG AGT G CT GAA GAC TTA GCT AAA     2079
Val Glu Arg Met Val Ser Pro Ile Glu Ser A la Glu Asp Leu Ala Lys
630                 635                 640                 645

CAG ACT GAA ATT GCA TAT GGG ACC CTG GAC T CC GGT TCA ACA AAA GAA     2127
Gln Thr Glu Ile Ala Tyr Gly Thr Leu Asp S er Gly Ser Thr Lys Glu
            650                 655                 660

TTT TTC AGA AGA TCC AAA ATT GCT GTG TAC G AG AAA ATG TGG TCT TAC     2175
Phe Phe Arg Arg Ser Lys Ile Ala Val Tyr G lu Lys Met Trp Ser Tyr
            665                 670                 675

ATG AAA TCA GCG GAG CCA TCT GTG TTT ACC A AA ACA ACA GCA GAC GGA     2223
Met Lys Ser Ala Glu Pro Ser Val Phe Thr L ys Thr Thr Ala Asp Gly
            680                 685                 690

GTG GCC CGA GTG CGA AAG TCC AAG GGA AAG T TC GCC TTC CTG CTG GAG     2271
Val Ala Arg Val Arg Lys Ser Lys Gly Lys P he Ala Phe Leu Leu Glu
            695                 700                 705

TCA ACC ATG AAT GAG TAC ATT GAG CAG AGA A AA CCA TGT GAT ACG ATG     2319
Ser Thr Met Asn Glu Tyr Ile Glu Gln Arg L ys Pro Cys Asp Thr Met
710                 715                 720                 725

AAA GTT GGT GGA AAT CTG GAT TCC AAA GGC T AT GGT GTG GCA ACC CCT     2367
Lys Val Gly Gly Asn Leu Asp Ser Lys Gly T yr Gly Val Ala Thr Pro
            730                 735                 740

AAA GGC TCA GCA TTA GGA ACG CCT GTA AAC C TT GCA GTA TTG AAA CTC     2415
Lys Gly Ser Ala Leu Gly Thr Pro Val Asn L eu Ala Val Leu Lys Leu
            745                 750                 755

AGT GAA CAA GGC ATC TTA GAC AAG CTG AAA A AC AAA TGG TGG TAC GAT     2463
Ser Glu Gln Gly Ile Leu Asp Lys Leu Lys A sn Lys Trp Trp Tyr Asp
            760                 765                 770

AAG GGG GAA TGT GGA GCC AAG GAC TCC GGG A GT AAG GAC AAG ACC AGC     2511
Lys Gly Glu Cys Gly Ala Lys Asp Ser Gly S er Lys Asp Lys Thr Ser
            775                 780                 785

GCT CTG AGC CTG AGC AAT GTG GCA GGC GTT T TC TAT ATA CTT GTC GGA     2559
Ala Leu Ser Leu Ser Asn Val Ala Gly Val P he Tyr Ile Leu Val Gly
790                 795                 800                 805

GGT CTG GGG CTG GCC ATG ATG GTG GCT TTG A TA GAA TTC TGT TAC AAA     2607
Gly Leu Gly Leu Ala Met Met Val Ala Leu I le Glu Phe Cys Tyr Lys
            810                 815                 820

TCA CGG GCA GAG TCC AAA CGC ATG AAA CTC A CA AAG AAC ACC CAA AAC     2655
Ser Arg Ala Glu Ser Lys Arg Met Lys Leu T hr Lys Asn Thr Gln Asn
            825                 830                 835

TTT AAG CCT GCT CCT GCC ACC AAC ACT CAG A AT TAT GCT ACA TAC AGA     2703
Phe Lys Pro Ala Pro Ala Thr Asn Thr Gln A sn Tyr Ala Thr Tyr Arg
            840                 845                 850

GAA GGC TAC AAC GTG TAT GGA ACA GAG AGT G TT AAG ATC TAGGGATCCC     2752
Glu Gly Tyr Asn Val Tyr Gly Thr Glu Ser V al Lys Ile
            855                 860                 865

TTCCCACTGG AGGCATGTGA TGAGAGGAAA TCACCGAAAA CGTGGCTGCT T CAAGGATCC     2812

TGAGCCAGAT TCACTCTCC TTGGTGTCGG GCATGACACG AATATTGCTG A TGGTGCAAT     2872

GACCTTTCAA TAGGAAAAAC TGATTTTTTT TTTCCTTCAG TGCCTTATGG A ACACTCTGA     2932

GACTCGCGAC AATGCAAACC ATCATTGAAA TCTTTTTGCT TTGCTTGAAA A AAAATAATT     2992
```

```
AAAATAAAAA CCAACAAAAA TGGACATGCA TCAAACCCTT GATGTATTAA T ATTTATTAT    3052

AGTTTTCATT AGGAATTC                                                   3070
```

(2) INFORMATION FOR SEQ ID NO:4:

(i) SEQUENCE CHARACTERISTICS:
        (A) LENGTH: 888 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Gln Ser Val Leu Arg Ala Val Phe P he Leu Val Leu Gly Leu
-22         -20                 -15              -10

Leu Gly His Ser His Gly Gly Phe Pro Asn T hr Ile Ser Ile Gly Gly
    -5              1               5                       10

Leu Phe Met Arg Asn Thr Val Gln Glu His S er Ala Phe Arg Phe Ala
            15                  20                  25

Val Gln Leu Tyr Asn Thr Asn Gln Asn Thr T hr Glu Lys Pro Phe His
            30                  35                  40

Leu Asn Tyr His Val Asp His Leu Asp Ser S er Asn Ser Phe Ser Val
            45                  50                  55

Thr Asn Ala Phe Cys Ser Gln Phe Ser Arg G ly Val Tyr Ala Ile Phe
            60              65                  70

Gly Phe Tyr Asp Gln Met Ser Met Asn Thr L eu Thr Ser Phe Cys Gly
 75             80                  85                      90

Ala Leu His Thr Ser Phe Val Thr Pro Ser P he Pro Thr Asp Ala Asp
            95                  100                 105

Val Gln Phe Val Ile Gln Met Arg Pro Ala L eu Lys Gly Ala Ile Leu
            110                 115                 120

Ser Leu Leu Gly His Tyr Lys Trp Glu Lys P he Val Tyr Leu Tyr Asp
            125                 130                 135

Thr Glu Arg Gly Phe Ser Ile Leu Gln Ala I le Met Glu Ala Ala Val
            140                 145                 150

Gln Asn Asn Trp Gln Val Thr Ala Arg Ser V al Gly Asn Ile Lys Asp
155             160                 165                     170

Val Gln Glu Phe Arg Arg Ile Ile Glu Glu M et Asp Arg Arg Gln Glu
            175                 180                 185

Lys Arg Tyr Leu Ile Asp Cys Glu Val Glu A rg Ile Asn Thr Ile Leu
            190                 195                 200

Glu Gln Val Val Ile Leu Gly Lys His Ser A rg Gly Tyr His Tyr Met
            205                 210                 215

Leu Ala Asn Leu Gly Phe Thr Asp Ile Leu L eu Glu Arg Val Met His
            220                 225                 230

Gly Gly Ala Asn Ile Thr Gly Phe Gln Ile V al Asn Asn Glu Asn Pro
235             240                 245                     250

Met Val Gln Gln Phe Ile Gln Arg Trp Val A rg Leu Asp Glu Arg Glu
            255                 260                 265

Phe Pro Glu Ala Lys Asn Ala Pro Leu Lys T yr Thr Ser Ala Leu Thr
            270                 275                 280

His Asp Ala Ile Leu Val Ile Ala Glu Ala P he Arg Tyr Leu Arg Arg
            285                 290                 295

Gln Arg Val Asp Val Ser Arg Arg Gly Ser A la Gly Asp Cys Leu Ala
            300                 305                 310
```

```
Asn Pro Ala Val Pro Trp Ser Gln Gly Ile Asp Ile Glu Arg Ala Leu
315                 320                 325                 330

Lys Met Val Gln Val Gln Gly Met Thr Gly Asn Ile Gln Phe Asp Thr
            335                 340                 345

Tyr Gly Arg Arg Thr Asn Tyr Thr Ile Asp Val Tyr Glu Met Lys Val
        350                 355                 360

Ser Gly Ser Arg Lys Ala Gly Tyr Trp Asn Glu Tyr Glu Arg Phe Val
    365                 370                 375

Pro Phe Ser Asp Gln Gln Ile Ser Asn Asp Ser Ala Ser Glu Asn
380                 385                 390

Arg Thr Ile Val Val Thr Thr Ile Leu Glu Ser Pro Tyr Val Met Tyr
395                 400                 405                 410

Lys Lys Asn His Glu Gln Leu Glu Gly Asn Glu Arg Tyr Glu Gly Tyr
            415                 420                 425

Cys Val Asp Leu Ala Tyr Glu Ile Ala Lys His Val Arg Ile Lys Tyr
        430                 435                 440

Lys Leu Ser Ile Val Gly Asp Gly Lys Tyr Gly Ala Arg Asp Pro Glu
    445                 450                 455

Thr Lys Ile Trp Asn Gly Met Val Gly Glu Leu Val Tyr Gly Arg Ala
460                 465                 470

Asp Ile Ala Val Ala Pro Leu Thr Ile Thr Leu Val Arg Glu Glu Val
475                 480                 485                 490

Ile Asp Phe Ser Lys Pro Leu Met Ser Leu Gly Ile Ser Ile Met Ile
            495                 500                 505

Lys Lys Pro Gln Lys Ser Lys Pro Gly Val Phe Ser Phe Leu Asp Pro
        510                 515                 520

Leu Ala Tyr Glu Ile Trp Met Cys Ile Val Phe Ala Tyr Ile Gly Val
    525                 530                 535

Ser Val Val Leu Phe Leu Val Ser Arg Phe Ser Pro Tyr Glu Trp His
540                 545                 550

Leu Glu Asp Asn Asn Glu Glu Pro Arg Asp Pro Gln Ser Pro Pro Asp
555                 560                 565                 570

Pro Pro Asn Glu Phe Gly Ile Phe Asn Ser Leu Trp Phe Ser Leu Gly
            575                 580                 585

Ala Phe Met Gln Gln Gly Cys Asp Ile Ser Pro Arg Ser Leu Ser Gly
        590                 595                 600

Arg Ile Val Gly Gly Val Trp Trp Phe Phe Thr Leu Ile Ile Ile Ser
    605                 610                 615

Ser Tyr Thr Ala Asn Leu Ala Ala Phe Leu Thr Val Glu Arg Met Val
620                 625                 630

Ser Pro Ile Glu Ser Ala Glu Asp Leu Ala Lys Gln Thr Glu Ile Ala
635                 640                 645                 650

Tyr Gly Thr Leu Asp Ser Gly Ser Thr Lys Glu Phe Phe Arg Arg Ser
            655                 660                 665

Lys Ile Ala Val Tyr Glu Lys Met Trp Ser Tyr Met Lys Ser Ala Glu
        670                 675                 680

Pro Ser Val Phe Thr Lys Thr Thr Ala Asp Gly Val Ala Arg Val Arg
    685                 690                 695

Lys Ser Lys Gly Lys Phe Ala Phe Leu Leu Glu Ser Thr Met Asn Glu
700                 705                 710

Tyr Ile Glu Gln Arg Lys Pro Cys Asp Thr Met Lys Val Gly Gly Asn
715                 720                 725                 730

Leu Asp Ser Lys Gly Tyr Gly Val Ala Thr Pro Lys Gly Ser Ala Leu
```

```
                         735                 740                 745
Gly Thr Pro Val Asn Leu Ala Val Leu Lys L eu Ser Glu Gln Gly Ile
                750                 755                 760
Leu Asp Lys Leu Lys Asn Lys Trp Trp Tyr A sp Lys Gly Glu Cys Gly
            765                 770                 775
Ala Lys Asp Ser Gly Ser Lys Asp Lys Thr S er Ala Leu Ser Leu Ser
        780                 785                 790
Asn Val Ala Gly Val Phe Tyr Ile Leu Val G ly Gly Leu Gly Leu Ala
795                 800                 805                 810
Met Met Val Ala Leu Ile Glu Phe Cys Tyr L ys Ser Arg Ala Glu Ser
                815                 820                 825
Lys Arg Met Lys Leu Thr Lys Asn Thr Gln A sn Phe Lys Pro Ala Pro
            830                 835                 840
Ala Thr Asn Thr Gln Asn Tyr Ala Thr Tyr A rg Glu Gly Tyr Asn Val
        845                 850                 855
Tyr Gly Thr Glu Ser Val Lys Ile
860                 865
```

(2) INFORMATION FOR SEQ ID NO:5:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:5:

```
Gly Ser Ala Leu Gly Asn Ala Val Asn Leu A la Val Leu Lys Leu Asn
1               5                   10                  15
Glu Gln Gly Leu Leu Asp Lys Leu Lys Asn L ys Trp Trp Tyr Asp Lys
                20                  25                  30
Gly Glu Cys Gly Ser Gly Gly Gly Asp Ser L ys Asp Lys Thr
            35                  40                  45
```

(2) INFORMATION FOR SEQ ID NO:6:

(i) SEQUENCE CHARACTERISTICS:
        (A) LENGTH: 46 amino acids
        (B) TYPE: amino acid
        (D) TOPOLOGY: linear (ii) MOLECULE TYPE: peptide (xi) SEQUENCE DESCRIPTION: SEQ ID NO:6:

```
Gly Ser Ala Leu Gly Thr Pro Val Asn Leu A la Val Leu Lys Leu Ser
1               5                   10                  15
Glu Gln Gly Ile Leu Asp Lys Leu Lys Asn L ys Trp Trp Tyr Asp Lys
                20                  25                  30
Gly Glu Cys Gly Ala Lys Asp Ser Gly Ser L ys Asp Lys Thr
            35                  40                  45
```

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Syntheti c DNA oligonucleotide (xi) SEQUENCE DESCRIPTION: SEQ ID NO:7:

ACACTCAGAA TTACGCTACA TACAGAGAAG GCTACAACGT 40